US012589160B2

(12) United States Patent
Biggar et al.

(10) Patent No.: US 12,589,160 B2

(45) Date of Patent: Mar. 31, 2026

(54) PEPTIDE-DERIVED THERAPEUTICS TARGETING KDM5C FOR THE TREATMENT OF CANCER

(71) Applicant: NUVOBIO CORPORATION, Ottawa (CA)

(72) Inventors: Kyle Kevin Biggar, Nepean (CA); Hemanta Adhikary, Nepean (CA); Matthew Jacob Hoekstra, Georgetown (CA)

(73) Assignee: NUVOBIO CORPORATION (CA)

( * ) Notice: Subject to any disclaimer, the term of this patent is extended or adjusted under 35 U.S.C. 154(b) by 367 days.

(21) Appl. No.: 17/438,925

(22) PCT Filed: Mar. 12, 2020

(86) PCT No.: PCT/CA2020/050332

§ 371 (c)(1),
(2) Date: Sep. 13, 2021

(87) PCT Pub. No.: WO2020/186345

PCT Pub. Date: Sep. 24, 2020

(65) Prior Publication Data

US 2022/0184221 A1 Jun. 16, 2022

Related U.S. Application Data

(60) Provisional application No. 62/818,793, filed on Mar. 15, 2019.

(51) Int. Cl.

| | |
|---|---|
| ***C07K 7/06*** | (2006.01) |
| ***A61K 47/64*** | (2017.01) |
| ***A61P 35/00*** | (2006.01) |
| ***C07K 7/08*** | (2006.01) |
| ***C12N 9/02*** | (2006.01) |
| *A61K 38/00* | (2006.01) |

(52) U.S. Cl.

CPC ............ *A61K 47/645* (2017.08); *A61P 35/00* (2018.01); *C07K 7/06* (2013.01); *C07K 7/08* (2013.01); *C12N 9/0071* (2013.01); *A61K 38/00* (2013.01); *C07K 2319/10* (2013.01); *C12Y 114/11* (2013.01)

(58) Field of Classification Search

CPC ....... A61K 47/645; A61K 38/00; A61P 35/00; C07K 7/06; C07K 7/08; C07K 2319/10; C12N 9/0071; C12Y 114/11

See application file for complete search history.

(56) References Cited

U.S. PATENT DOCUMENTS

2006/0041105 A1* 2/2006 Jiang .................... A61K 51/088 530/324

FOREIGN PATENT DOCUMENTS

| | | |
|---|---|---|
| WO | WO2006/125134 | 11/2006 |
| WO | WO2017/194958 | 11/2017 |

OTHER PUBLICATIONS

Uniprot_2017, (see A0A1SHYUB, Uniprot database, Apr. 12, 2017) (Year: 2017).*

Arrowsmith,C. H. et al. "Epigenetic protein families: a new frontier for drug discovery" Nat. Rev. Drug Discov. 2012; 11, 384-400.

Beck-Sickinger, A. G. et al. "Posttranslational Modification of Proteins. Expanding Nature's Inventory" By Christopher T. Walsh, Angew. Chem. Int. Ed. 2006; 45, p. 1020.

Biggar, K. et al. "Non-histone protein methylation as a regulator of cellular signaling and function" Nat. Rev. Mol. Cell Biol. 2015; 16, 5-17.

Blum, G. et al. "Small-molecule inhibitors of Set8 with cellular activity" ACS Chem. Biol. 2014; 9:2471-2478.

Derakhshankhah, H. et al. "Cell penetrating peptides: A concise review with emphasis on biomedical Applications" Biomedicine and Pharmacotherapy, Sep. 2018 vol. 108:1090-1096.

Dhami, G. et al. "Dynamic methylation of Numb by Set8 regulates its binding to p53 and apoptosis" Mol Cell. 2013;50(4):565-76.

Ding, C. et al. "A polymorphism at the miR-502 binding site in the 3' untranslated region of the Set8 gene is associated with the outcome of small-cell lung cancer" Experimental and therapeutic medicine. 2012;3(4):689-92.

Guo, Z. et al. "A polymorphism at the miR-502 binding site in the 3'-untranslated region of the histone methyltransferase Set8 is associated with hepatocellular carcinoma outcome" Int J Cancer. 2012;131(6):1318-22.

Hamamoto, R. et al. "Critical roles of non-histone protein lysine methylation in human tumorigenesis" Nat. Rev. Cancer 2015; 15, 110-124.

Hashemi, M. et al. "Association of functional polymorphism at the miR-502-binding site in the 3' untranslated region of the SET8 gene with risk of childhood acute lymphoblastic leukemia, a preliminary report" Tumor Biol. 2014;35(10): 10375-9.

Ji, X. et al. "Lysine-specific demethylase 5C promotes hepatocellular carcinoma cell invasion through inhibition BMP7 expression" BMC Cancer 2015; 15: 801, 1-15.

Jin, H. et al. "Protein modifications as potential biomarkers in breast cancer" Biomark. Insights 2009; 4, 191-200.

Rao,R. et al. "Hijacked in cancer: the KMT2(MLL) family of methyltransferases" Nat. Rev. Cancer 2015; 15, 334-346.

Seo, J. et al. "Post-translational modifications and their biological functions: proteomic analysis and systematic approaches" J. Biochem. Mol. Biol. 2004; 37, 35-44.

Shi, X. et al. "Modulation of p53 function by Set8-mediated methylation at lysine 382" Mol Cell. 2007;27(4):636-46.

Song, F et al. "An miR-502-binding site single-nucleotide polymorphism in the 3'-untranslated region of the SET8 gene is associated with early age of breast cancer onset" Clin Cancer Res. 2009;15(19):6292-300.

Stein, J. et al. "KDM5C is overexpressed in prostate cancer and is a prognostic marker for prostate-specific antigen-relapse following radical prostatectomy" Am. J. Pathol. 2014; 184: 2430-2437.

Takawa, M. et al. "Histone lysine methyltransferase SET8 promotes carcinogenesis by deregulating PCNA expression" Cancer Res. 2012;72(13):3217-27.

(Continued)

*Primary Examiner* — Sudhakar Katakam

(74) *Attorney, Agent, or Firm* — Husch Blackwell LLP

(57) ABSTRACT

The present invention relates to treatment of cancer. In particular, the present invention relates to peptides that bind KDM5C for the treatment of cancer.

6 Claims, 6 Drawing Sheets

Specification includes a Sequence Listing.

(56) References Cited

OTHER PUBLICATIONS

Valente, S. et al. "Identification of PR-SET7 and EZH2 selective inhibitors inducing cell death in human leukemia U937 cells" Biochimie. 2012;94(11):2308-13.
Veschi, V. et al. "Epigenetic siRNA and chemical screens identify Set8 inhibition as a therapeutic strategy for p53 activation in high-risk neuroblastoma" Cancer Cell 2017;31:50-63.
Vinogradova,M. et al. (2016) "An inhibitor of KDM5 demethylases reduces survival of drug-tolerant cancer cells" Nat. Chem. Biol. 12(7): 531-538.
Wang, C. et al. "A polymorphism at the miR-502 binding site in the 3' untranslated region of the SET8 gene is associated with the risk of epithelial ovarian cancer" Cancer Genetics. 2012;205(7-8): 373-6.
Wang, Q. et al. "Histone demethylase JARIDIC promotes breast cancer metastasis cells via down regulating BRMS1 expression" Biochem. Biophys. Res. Commun. 2015; 464: 659-666.
Xu, J. et al. "Genetic variation in a microRNA-502 minding site in SET8 gene confers clinical outcome of non-small cell lung cancer in a Chinese population" PLoS One. 2013;8(10):e77024. p. 1-9.
Xu, L. et al. "Enhancement of proliferation and invasion of gastric cancer cell by KDM5C via decrease in p53 expression" Technol. Cancer Res. Treat. 2017; 16:141-149.
Yang, F. et al. "SET8 promotes epithelial mesenchymal transition and confers TWIST dual transcriptional activities" EMBO J. 2012;31(1):110-23.
Yao, L. et al. "Histone H4 Lys 20 methyltransferase SET8 promotes androgen receptor-mediated transcription activation in prostate cancer" Biochem Biophys Res Commun. 2014;450(1):692-6.
Zhang, X. et al. "Lysine methylation: beyond histones" Acta Biochim. Biophys. Sin. 2012; 44, 14-27.

* cited by examiner

PEPTIDE-DERIVED THERAPEUTICS TARGETING KDM5C FOR THE TREATMENT OF CANCER

CROSS-REFERENCE TO RELATED APPLICATIONS

This application claims priority to and is a 35 U.S.C. § 371 national phase application of PCT/CA2020/050332 (WO 2020/186345), filed on Mar. 12, 2020, entitled "Peptide-Derived Therapeutics Targeting KDM5C for the Treatment of Cancer", which application claims the benefit of U.S. Provisional Application Ser. No. 62/818,793, filed Mar. 15, 2019, which are incorporated herein by reference in their entirety.

SEQUENCE STATEMENT

Incorporated by reference herein in its entirety is the Sequence Listing text document entitled "0238_3810_104PCTUS", size of 24 kilobytes.

FIELD OF THE INVENTION

The present invention relates to treatment of cancer. In particular, the present invention relates to peptide-derived therapeutics for the treatment of cancer.

BACKGROUND

Two of every five Canadians are diagnosed with cancer at some point in their lives (Canadian Cancer Society, Cancer Statistics 2016). For the majority of cancers, targeted therapies are not yet available. For example, systemic chemotherapy is the only treatment option for triple negative breast cancer after surgery. However, chemotherapy is highly toxic and cancer cells can eventually become resistant to the treatment.

It is known that one gene mutation or one protein dysfunction does not initiate the development of cancer, but rather it is the dysregulation of a system of proteins that initiate the process and drives progression. As a result, there is an urgent need to understand the mechanism of cancer progression and chemoresistance in order to develop strategies to overcome resistance. Lysine methylation is essential in regulating many biological processes that range from growth and proliferation to pathological conditions, such as neurodegenerative disease, intellectual disability, and cancer. Given the extensive regulatory importance realized for lysine methylation, any mutations or dysfunction in methyltransferase (KMT) or demethylase (KDM) enzymes (i.e., the enzymes that catalyze the addition/removal of lysine methylation) can lead to deregulated cell function, tumourigenesis and chemotherapy resistance (Arrowsmith et al., 2012; Hanamoto et al., 2015; Rao and Dou, 2015).

The realization that lysine methylation plays a critical role in the development of many human diseases is perhaps not a surprising one. It is well established that dynamic post-translational modifications (PTMs) made to protein, such as phosphorylation and methylation, play a crucial role in the transmission of biological signals (Seo and Lee, 2004; Beck-Sickinger and Mörl, 2006; Zhang et al., 2012). These small chemical protein modifications allow for cells to exert greater control over specific cellular processes, while dysfunction within this PTM network are common drivers of cancer development and progression (Jin and Zangar, 2009). Dysfunction in the dynamic lysine methylation network (currently consisting of >5000 different lysine methylation modifications) has been identified as a prominent contributor to the development of many different types of cancer. Given the involvement of lysine methylation in a growing number of different biological processes (Biggar and Li, 2015), methyl-modifying enzymes are emerging as a promising drug target.

To date, only a handful of KMT and KDM inhibitors have been discovered or developed, with almost all inhibitors currently within the preclinical stages of development (Hanamoto et al., 2015). Indeed, given the similarity between catalytic domains among families of these enzymes, it has been difficult to develop a small molecule inhibitor that is specific for a dysfunctional enzyme without significant off-target effects. Given the potential for substantial off-target toxicity, there is a critical need for more refined, enzyme-specific, inhibitors to be developed. Peptide-based therapeutics may be designed with exquisite specificity for their targets. This results in fewer side-effects from treatment. Peptide-based drugs also offer good efficacy, tolerability, predicted metabolism, lower attrition rates, and the advantage of a standard synthesis protocol.

SUMMARY OF THE INVENTION

An object of the present invention is to provide peptide-derived therapeutics targeting KDM5C for the treatment of cancer. In one aspect of the present invention, there is provided a peptide that binds to KDM5C.

In another aspect of the present invention, there is provided a peptide that binds to KDM5C, wherein said peptide comprises the sequence:

$X_1X_2X_3X_4X_5X_6X_7X_8X_9$; where
$X_1$=T or S
$X_2$=D, E or I
$X_3$=T, D or Q
$X_4$=Q, S, N or T
$X_5$=K or Nle
$X_6$=T
$X_7$=H
$X_8$=H
$X_9$=H; or a binding fragment thereof (SEQ ID NO:65).

In accordance with another aspect of the invention, there is provided a peptide that binds to KDM5C and comprises the sequence selected from the group consisting of T D T T K T H H H (SEQ ID NO:1); T D T Q K T H H H (SEQ ID NO:2); T D T N K T H H H (SEQ ID NO:3); T E D S K T H H H (SEQ ID NO:4); T E D Q K T H H H (SEQ ID NO:5); T T Q S K T H H H (SEQ ID NO:6); T D T S K T H H H (SEQ ID NO:7); T E D T K T H H H (SEQ ID NO:8); T E E Q K T H H H (SEQ ID NO:9); S D Q Q K T H H H (SEQ ID NO:10); T T Q Q K T H H H (SEQ ID NO:11); S D Q T K T H H H (SEQ ID NO:12); T D D Q K T H H H (SEQ ID NO:13); T E E N K T H H H (SEQ ID NO:14); T E E S K T H H H (SEQ ID NO:15); T T Q T K T H H H (SEQ ID NO:16); T D S T K T H H H (SEQ ID NO:17); S E T Q K T H H H (SEQ ID NO:18); S E T S K T H H H (SEQ ID NO:19); T D D N K T H H H (SEQ ID NO:20); T D T T n T H H H (SEQ ID NO:21); T D T Q n T H H H (SEQ ID NO:22); T D T N n T H H H (SEQ ID NO:23); T E D S n T H H H (SEQ ID NO:24); T E D Q n T H H H (SEQ ID NO:25); T T Q S n T H H H (SEQ ID NO:26); T D T S n T H H H (SEQ ID NO:27); T E D T n T H H H (SEQ ID NO:28); T E E Q n T H H H (SEQ ID NO:29); S D Q Q n T H H H (SEQ ID NO:30); T T Q Q n T H H H (SEQ ID NO:31); S D Q T n T H H H (SEQ ID NO:32); T D D Q n T H H H (SEQ ID NO:33); T E E N n T H H H (SEQ ID NO:34); T E E S n T H H H (SEQ ID NO:35); T T Q T n T H H H (SEQ ID NO:36); T D S T n T H H H (SEQ ID NO:37); S E T Q n T H H H (SEQ ID NO:38); S E T S n T H H H (SEQ ID NO:39); T D D N n T H H H (SEQ ID NO:40); R T K Q T A R K S T G G (SEQ ID NO:41); R T n Q T A R K S T G G (SEQ ID NO:42); G A K R H R K V L R D N I (SEQ ID NO:43) and G A K R H R n V L R D N I (SEQ ID NO:44); wherein n=norLeucine (Nle) or a binding fragment thereof.

In accordance with another aspect of the invention, there is provided a peptide that binds to KDM5C, wherein said peptide comprises the sequence:

$X_1X_2X_3X_4X_5X_6X_7X_8$ $X_9$; where $X_1$=T $X_2$=K, G, L, Q, V, E, H or I $X_3$=I, L, V or D $X_4$=L, M, V, F or S $X_5$=V or K $X_6$=V, G, R, L, K, F, H, T, A, P or N $X_7$=H $X_8$=H $X_9$=H; or a binding fragment thereof (SEQ ID NO:66)

In accordance with another aspect of the invention, there is provided a peptide comprising the sequence selected from the group consisting of:

```
                                (SEQ ID NO: 23)
TDTNnTHHH

                                (SEQ ID NO: 45)
{6-aminohexanoic acid}GRKKRRQRRRPPQ;

                                (SEQ ID NO: 2)
TDTQKTHHH

                                (SEQ ID NO: 45)
{6-aminohexanoic acid}GRKKRRQRRRPPQ;

                                (SEQ ID NO: 3)
TDTNKTHHH

                                (SEQ ID NO: 45)
{6-aminohexanoic acid}GRKKRRQRRRPPQ;

                                (SEQ ID NO: 27)
TDTSnTHHH

                                (SEQ ID NO: 45)
{6-aminohexanoic acid}GRKKRRQRRRPPQ;

                                (SEQ ID NO: 4)
TEDSKTHHH

                                (SEQ ID NO: 45)
{6-aminohexanoic acid}GRKKRRQRRRPPQ;

                                (SEQ ID NO: 7)
TDTSKTHHH

                                (SEQ ID NO: 45)
{6-aminohexanoic acid}GRKKRRQRRRPPQ;

                                (SEQ ID NO: 40)
TDTTnTHHH

                                (SEQ ID NO: 45)
{6-aminohexanoic acid}GRKKRRQRRRPPQ;

                                (SEQ ID NO: 25)
TEDQnTHHH

                                (SEQ ID NO: 45)
{6-aminohexanoic acid}GRKKRRQRRRPPQ;
```

-continued

```
                                (SEQ ID NO: 6)
TTQSKTHHH

                                (SEQ ID NO: 45)
{6-aminohexanoic acid}GRKKRRQRRRPPQ;

                                (SEQ ID NO: 5)
TEDQKTHHH

                                (SEQ ID NO: 45)
{6-aminohexanoic acid}GRKKRRQRRRPPQ;

                                (SEQ ID NO: 44)
GAKRHRnVLRDNI

                                (SEQ ID NO: 45)
{6-aminohexanoic acid}GRKKRRQRRRPPQ;

                                (SEQ ID NO: 38)
SETQnTHHH

                                (SEQ ID NO: 45)
{6-aminohexanoic acid}GRKKRRQRRRPPQ;

                                (SEQ ID NO: 10)
SDQQKTHHH

                                (SEQ ID NO: 45)
{6-aminohexanoic acid}GRKKRRQRRRPPQ;

                                (SEQ ID NO: 23)
TDTNnTHHH

                                (SEQ ID NO: 49)
{6-aminohexanoic acid}FFLIPKGRRRRRRRRR;

                                (SEQ ID NO: 2)
TDTQKTHHH

                                (SEQ ID NO: 49)
{6-aminohexanoic acid}FFLIPKGRRRRRRRRR;

                                (SEQ ID NO: 3)
TDTNKTHHH

                                (SEQ ID NO: 49)
{6-aminohexanoic acid}FFLIPKGRRRRRRRRR;

                                (SEQ ID NO: 27)
TDTSnTHHH

                                (SEQ ID NO: 49)
{6-aminohexanoic acid}FFLIPKGRRRRRRRRR;

                                (SEQ ID NO: 4)
TEDSKTHHH

                                (SEQ ID NO: 49)
{6-aminohexanoic acid}FFLIPKGRRRRRRRRR;

                                (SEQ ID NO: 7)
TDTSKTHHH

                                (SEQ ID NO: 49)
{6-aminohexanoic acid}FFLIPKGRRRRRRRRR;

                                (SEQ ID NO: 40)
TDTTnTHHH

                                (SEQ ID NO: 49)
{6-aminohexanoic acid}FFLIPKGRRRRRRRRR;

                                (SEQ ID NO:)
TEDQnTHHH

                                (SEQ ID NO: 49)
{6-aminohexanoic acid}FFLIPKGRRRRRRRRR;

                                (SEQ ID NO: 6)
TTQSKTHHH
```

-continued (SEQ ID NO: 49)
{6-aminohexanoic acid}FFLIPKGRRRRRRRRR;

(SEQ ID NO: 5)
TEDQKTHHH (SEQ ID NO: 49)
{6-aminohexanoic acid}FFLIPKGRRRRRRRRR;

(SEQ ID NO: 44)
GAKRHRnVLRDNI (SEQ ID NO: 49)
{6-aminohexanoic acid}FFLIPKGRRRRRRRRR;

(SEQ ID NO: 38)
SETQnTHHH (SEQ ID NO: 49)
{6-aminohexanoic acid}FFLIPKGRRRRRRRRR;

(SEQ ID NO: 10)
SDQQKTHHH (SEQ ID NO: 49)
{6-aminohexanoic acid}FFLIPKGRRRRRRRRR;

(SEQ ID NO: 23)
TDTNnTHHH (SEQ ID NO: 50)
{6-aminohexanoic acid}RRWRRWRRWRR;

(SEQ ID NO: 2)
TDTQKTHHH (SEQ ID NO: 50)
{6-aminohexanoic acid}RRWRRWRRWRR;

(SEQ ID NO: 3)
TDTNKTHHH (SEQ ID NO: 50)
{6-aminohexanoic acid}RRWRRWRRWRR;

(SEQ ID NO: 27)
TDTSnTHHH (SEQ ID NO: 50)
{6-aminohexanoic acid}RRWRRWRRWRR;

(SEQ ID NO: 4)
TEDSKTHHH (SEQ ID NO: 50)
{6-aminohexanoic acid}RRWRRWRRWRR;

(SEQ ID NO: 7)
TDTSKTHHH (SEQ ID NO: 50)
{6-aminohexanoic acid}RRWRRWRRWRR;

(SEQ ID NO: 40)
TDTTnTHHH (SEQ ID NO: 50)
{6-aminohexanoic acid}RRWRRWRRWRR;

(SEQ ID NO:)
TEDQnTHHH (SEQ ID NO: 50)
{6-aminohexanoic acid}RRWRRWRRWRR;

(SEQ ID NO: 6)
TTQSKTHHH (SEQ ID NO: 50)
{6-aminohexanoic acid}RRWRRWRRWRR;

-continued (SEQ ID NO: 5)
TEDQKTHHH (SEQ ID NO: 50)
{6-aminohexanoic acid}RRWRRWRRWRR;

(SEQ ID NO: 44)
GAKRHRnVLRDNI (SEQ ID NO: 50)
{6-aminohexanoic acid}RRWRRWRRWRR;

(SEQ ID NO: 38)
SETQnTHHH (SEQ ID NO: 50)
{6-aminohexanoic acid}RRWRRWRRWRR; and (SEQ ID NO: 10)
SDQQKTHHH (SEQ ID NO: 50)
{6-aminohexanoic acid}RRWRRWRRWRR.

In other aspects of the present invention, there is provided methods of inhibiting the activity of KDM5C in a subject in need thereof or methods of treating a disease associate with increased KDM5C, including but not limited to cancer, in a subject in need thereof, comprising administering one or more of the peptides of the invention.

DETAILED DESCRIPTION

Figure 1:
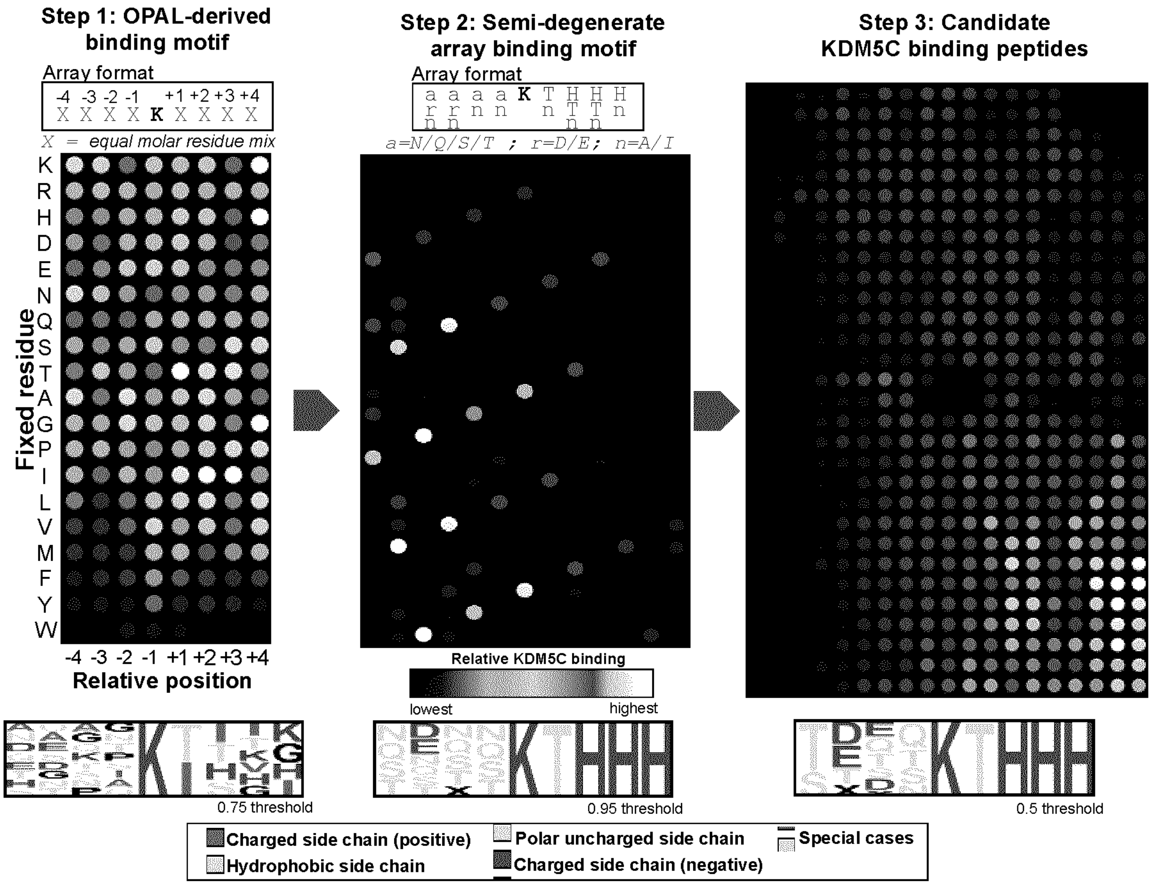
FIG. 1. Peptide array screening for the systematic identification of peptide sequences that display interaction with KDM5C. Relative KDM5C interaction with an oriented peptide array library (OPAL). The relative intensity suggests a positive selection for the substituted residue at a given position of the peptide. The OPAL is derived from a library with equimolar mix of amino acids within a degenerate sequence with position-specific fixed amino acids. Degeneracy is then reduced in subsequent peptide arrays. Sequence motifs indicate amino acid preference at positions relative to the central lysine.

The present invention relates to peptide-derived therapeutics targeting enzymes in the lysine methylation pathway and the use of such therapeutics to treat diseases or disorders associated with dysfunction in lysine methylation. In particular, the present invention relates to peptide-derived therapeutics which target KDM5C and the uses thereof.

Peptides:

The present invention provides peptides that bind, optionally specifically bind, to KDM5C. In specific embodiments, the peptides of the present invention bind KDM5C with high affinity. In specific embodiments, the peptides bind to KDM5C and inhibit activity thereof. In certain embodiments, the peptides bind the catalytic core of KDM5C.

Exemplary peptides are set forth in the table below:

| Experimental Peptide | SEQ ID NO: | Sequence |
|---|---|---|
| EP1 | 1 | T D T T K T H H H |
| EP2 | 2 | T D T Q K T H H H |
| EP3 | 3 | T D T N K T H H H |
| EP4 | 4 | T E D S K T H H H |
| EP5 | 5 | T E D Q K T H H H |
| EP6 | 6 | T T Q S K T H H H |
| EP7 | 7 | T D T S K T H H H |
| EP8 | 8 | T E D T K T H H H |
| EP9 | 9 | T E E Q K T H H H |
| EP10 | 10 | S D Q Q K T H H H |
| EP11 | 11 | T T Q Q K T H H H |
| EP12 | 12 | S D Q T K T H H H |
| EP13 | 13 | T D D Q K T H H H |
| EP14 | 14 | T E E N K T H H H |
| EP15 | 15 | T E E S K T H H H |
| EP16 | 16 | T T Q T K T H H H |
| EP17 | 17 | T D S T K T H H H |
| EP18 | 18 | S E T Q K T H H H |
| EP19 | 19 | S E T S K T H H H |
| EP20 | 20 | T D D N K T H H H |
| EP21 | 21 | T D T T n T H H H |
| EP22 | 22 | T D T Q n T H H H |
| EP23 | 23 | T D T N n T H H H |
| EP24 | 24 | T E D S n T H H H |
| EP25 | 25 | T E D Q n T H H H |
| EP26 | 26 | T T Q S n T H H H |
| EP27 | 27 | T D T S n T H H H |
| EP28 | 28 | T E D T N T H H H |
| EP29 | 29 | T E E Q n T H H H |
| EP30 | 30 | S D Q Q n T H H H |
| EP31 | 31 | T T Q Q n T H H H |
| EP32 | 32 | S D Q T n T H H H |
| EP33 | 33 | T D D Q n T H H H |
| EP34 | 34 | T E E N n T H H H |
| EP35 | 35 | T E E S n T H H H |
| EP36 | 36 | T T Q T n T H H H |

-continued

| Experimental Peptide | SEQ ID NO: | Sequence |
|---|---|---|
| EP37 | 37 | T D S T n T H H H |
| EP38 | 38 | S E T Q N T H H H |
| EP39 | 39 | S E T S n T H H H |
| EP40 | 40 | T D D N n T H H H |
| EP41 | 41 | R T K Q T A R K S T G G |
| EP42 | 42 | R T n Q T A R K S T G G |
| EP43 | 43 | G A K R H R K V L R D N I |
| EP44 | 44 | G A K R H R n V L R D N I |

n = norLeucine (Nle)

In certain embodiments of the present invention, the peptides comprise the consensus sequence set forth below:

$X_1X_2X_3X_4X_5$THHH (SEQ ID NO:65); where $X_1$=T or S $X_2$=D, E or I $X_3$=T, D or Q $X_4$=Q, S, N or T $X_5$=K or Nle In certain embodiments of the present invention, there is provided a peptide comprising the sequence as set forth in any one of SEQ ID NOs: 1-40.

In certain embodiments, the peptide inhibitors are modified from the natural substrate peptides of KDM5C. The natural substrate peptides of KDM5C include histones H3-K4 and H4-K20. In specific embodiments, the peptide inhibitors are histones H3-K4 and H4-K20 with Lys to nor-Leu mutations. In specific embodiments, the peptides comprise the sequence as set forth in any one of SEQ ID NOs: 41-44.

In certain embodiments of the present invention, there is provided peptides comprising variant sequences other than those specifically disclosed herein, which comprise significant sequence identity (e.g. 75%, 80%, 85%, 90%, 95%, 98%, or 99% sequence identity) to the amino acid sequence provided that such peptides retain the ability to inhibit KDM5C activity. Such peptides can comprise one or more amino acid substitutions, additions, deletions, or insertions as compared to the parent amino acid sequence. Conservative amino acid substitutions are known in the art, and include amino acid substitutions in which one amino acid having certain physical and/or chemical properties is exchanged for another amino acid that has the same or similar chemical or physical properties. For instance, the conservative amino acid substitution can be an acidic amino acid substituted for another acidic amino acid (e.g. Asp or Glu), an amino acid with a nonpolar side chain substituted for another amino acid with a nonpolar side chain (e.g. Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc. In certain embodiments, naturally occurring amino acids in the peptides are replaced with amino acid analogs and derivatives thereof.

A worker skilled in the art could readily determine amino acid substitutions or truncations which impact binding activity of the peptides of the present invention. In certain embodiments, there is provided the EP4 peptide (i.e. the peptide comprising T E D S K T H H H; (SEQ ID NO:4)) comprising one or more substitutions.

Figure 4:
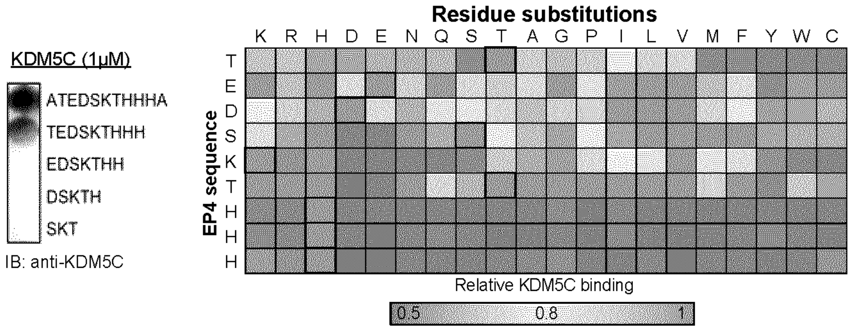
FIG. 4. Characterization of critical residues of the KDM5 inhibitor, EP4 by in vitro binding assay. (left) Progressive C-terminal and N-terminal tandem truncation of EP4. Spot intensity (dark) indicates relative interaction with KDM5C as detected by chemiluminescence. (right) Systematic mutation of the EP4 alters KDM5C binding activity. Relative binding preference of KDM5C was systematically determined in order to assess the possible amino acid mutations of the EP4 peptide that alter in vitro binding activity, either resulting in maintaining or strengthening (green), tolerable (yellow) or intolerable (red) KDM5C interaction. WT EP4 sequences are bolded.

FIG. 4 provides details with respect to the impact of substitutions on the binding activity of EP4. Following this systematic approach, position-specific tolerable mutations were identified. Accordingly, in certain embodiments, there is provided a peptide that binds to KDM5C, wherein said peptide comprises the sequence (SEQ ID NO:66):

$X_1X_2X_3X_4X_5X_6X_7X_8$ $X_9$; where $X_1$=T $X_2$=K, G, L, Q, V, E, H or I $X_3$=I, L, V or D $X_4$=L, M, V, F or S $X_5$=V or K $X_6$=V, G, R, L, K, F, H, T, A, P, I or N $X_7$=H $X_8$=H $X_9$=H.

In certain embodiments of the present invention, there is provided peptides comprising a fragment of the sequences specifically disclosed herein comprising at least 5 contiguous amino acids, provided that such peptides retain the ability to inhibit KDM5C activity.

In certain embodiments of the present invention, the peptides or fragments thereof comprise additional amino acids at the N and/or C terminus. In certain embodiments, the peptides of the present invention comprise A or AA at the N terminus. In certain embodiments, the peptides of the present invention comprise A or AA at the C terminus. In certain embodiments, the peptides of the present invention comprise A or AA at the N and C terminals. In certain embodiments of the present invention, there is provided a conjugate or fusion protein comprising the peptide of the present invention and heterologous amino acid sequence.

In certain embodiments, the peptides of the present invention includes a linker sequence. Linkers are known in the art and are generally classified into 3 categories according to their structures: (1) flexible linkers, (2) rigid linkers, and (3) in vivo cleavable linkers. Besides the basic role in linking the functional peptides together (as in flexible and rigid linkers) or releasing free functional peptide inhibitor in vivo (as in in vivo cleavable linkers), linkers may offer many other advantages for the production of inhibitor peptides, such as improving biological activity, increasing expression yield, and achieving desirable pharmacokinetic profiles.

| Linker | Model | Advantages | Example(s) |
|---|---|---|---|
| Flexible |  | Allows for interaction between functional peptide and delivery mechanism (i.e., functional units) | (GGGGS, SEQ ID NO: 67)n, (G)n, 6-aminohexanoic acid (i.e., ahx) |
| |  | Increases separation between functional units | |

-continued

| Linker | Model | Advantages | Example(s) |
|---|---|---|---|
| Rigid |  | Maintain distance between functional units | (EAAAK; SEQ ID NO: 68)n, (XP)n |
| Cleavable |  | Allows for in vivo separation of functional units | Disulphide, protease sensitive peptide sequences |

In certain embodiments, the peptides of the present Invention further comprise a 6-aminohexanoic acid linker. The chemical structure of the linker is set forth below:

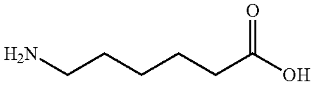

In specific embodiments, a cell penetrating peptide is conjugated to the peptide of the invention via a linker sequence.

In certain embodiments of the present invention, the peptides comprise other modifications including, without limitation, glycosylations, acetylations, phosphorylations, PEG, D-amino acids, nanoparticles, solid lipid nanoparticles, esterification, N-acetylation or may be formulated with liposomes, nano-emulsions, mucoadhesive polymers, nanoparticles, solid lipid nanoparticles.

It is known in the art that peptide modifications may improve therapeutic peptide delivery by increasing stability, inhibiting enzyme activity, enhancing absorption and/or cell targeting.

Mechanisms of Therapeutic Peptide Delivery

| Goal | Peptide modification/formulations |
|---|---|
| Stomach | |
| Increased stability | PEG, D-amino acids, nanoparticles, solid lipid nanoparticles |

-continued

| Goal | Peptide modification/formulations |
|---|---|
| Small intestine | |
| Increased stability | cyclization, PEG, lipidation, D-amino acids, polymer matrices, nanoparticles, esterification, N-acetylation |
| Enzyme inhibitors | soybean trypsin inhibitor, aprotinin, puromycin, bacitracin |
| Absorption enhancers | chitosans, fatty acids, lectins, Zonula occludens toxin, cell penetrating peptides, liposomes, nano-emulsions, mucoadhesive polymers, nanoparticles, solid lipid nanoparticles |
| Circulation | |
| Increased stability | PEG, hyper-glycosylation, liposomes, nanoparticles |
| Cell targeting | Antibody, cell penetrating peptides |

The peptides of the present invention may be coupled, either directly or via a linker, to a cell penetrating motif or other moiety so as to more efficiently facilitate the delivery of the peptide to the interior of a cell. Thus, the peptide can be provided as part of a composition or conjugate comprising the peptide and cell penetrating motif or other moiety. Any of various cell penetrating motifs and or other moieties useful for these purposes can be used. By way of illustration, suitable cell penetrating motifs and other relevant moieties (e.g. cell-membrane anchoring moieties) include lipids and fatty acids, cell penetrating peptides, and other types of carrier molecules (e.g. Pep-1).

In certain embodiments, the peptides of the present invention are coupled either directly or via a linker to a cell penetrating peptide. A repository of cell penetrating peptide can be found at crdd.osdd.net/Raghava/cppsite/index.html. Exemplary cell penetrating peptide are set forth in the table below:

| CPP name | Sequence | Origin | Class |
|---|---|---|---|
| TAT48-60 | GRKKRRQRRRPPQ (SEQ ID NO: 45) | HIV-1 TAT protein | Cationic |
| TAT49-57 | RKKRRQRRR (SEQ ID NO: 46) | HIV-1 TAT protein | Cationic |
| Penetratin, pAntp(43-58) | RQIKIWFQNRRMKWKK (SEQ ID NO: 47) | Antennapedia *Drosophila melanogaster* | Cationic |
| Polyarginines | Rn | Chemically synthesized | Cationic |
| DPV1047 | VKRGLKLRHVRPRVTRMDV (SEQ ID NO: 48) | Chemically synthesized | Cationic |
| PR9 | FFLIPKGRRRRRRRRR (SEQ ID NO: 49) | Chemically synthesized | Cationic |
| Mut6DPT (CPP) | RRWRRWRRWRR (SEQ ID NO: 50) | Chemically synthesized | Cationic |
| MPG | GALFLGFLGAAGSTMGAWSQPKKKRKV (SEQ ID NO: 51) | HIV glycoprotein 41/SV40 T antigen NLS | Amphipathic |
| Pep-1 | KETWWETWWTEWSQPKKKRKV (SEQ ID NO: 52) | Tryptophan-rich cluster/SV40 T antigen NLS | Amphipathic |

-continued

| CPP name | Sequence | Origin | Class |
|---|---|---|---|
| pVEC | LLIILRRRIRKQAHAHSK (SEQ ID NO: 53) | Vascular endothelial cadherin | Amphipathic |
| ARF(1-22) | MVRRFLVTLRIRRACGPPRVRV (SEQ ID NO: 54) | p14ARF protein | Amphipathic |
| BPrPr(1-28) | MVKSKIGSWILVLFVAMWSDVGLCKKRP (SEQ ID NO: 55) | N terminus of unprocessed bovine prion protein | Amphipathic |
| MAP | KLALKLALKALKAALKLA (SEQ ID NO: 56) | Chemically synthesized | Amphipathic |
| Transportan | GWTLNSAGYLLGKINLKALAALAKKIL (SEQ ID NO: 57) | Chimeric galanin-mastoparan | Amphipathic |
| p28 | LSTAADMQGVVTDGMASGLDKDYLKPDD (SEQ ID NO: 58) | Azurin | Amphipathic |
| VT5 | DPKGDPKGVTVTVTVTVTGKGDPKPD (SEQ ID NO: 59) | Chemically synthesized | Amphipathic |
| Bac 7 (Bac 1-24) | RRIRPRPPRLPRPRPRPLPFPRPG (SEQ ID NO: 60) | Bactenecin family of antimicrobial peptides | Amphipathic |
| C105Y | CSIPPEVKFNKPFVYLI (SEQ ID NO: 61) | α1-Antitrypsin | Hydrophobic |
| PFVYLI | PFVYLI (SEQ ID NO: 62) | Derived from synthetic C105Y | Hydrophobic |
| Pep-7 | SDLWEMMMVSLACQY (SEQ ID NO: 63) | CHL8 peptide phage clone | Hydrophobic |

Repository can be found at crdd.osdd.net/Raghava/cppsite/index.html

In certain embodiments of the present invention, a TAT cell penetrating peptide is linked either directly or via a linker to the peptides of the present invention. In certain embodiments of the present invention, a TAT cell penetrating peptide comprising the sequence GRKKRRQRRRPPQ is linked to the peptides of the present invention directly or via a linker. In certain embodiments of the present invention, a TAT cell penetrating peptide comprising the sequence GRKKRRQRRRPPQ (SEQ ID NO:45) is linked to the peptides of the present invention via a 6-aminohexanoic acid linker. In certain embodiments, the cell penetrating peptide is linked to the N-terminus of the peptide either directly or indirectly via a linker. In certain embodiments, the cell penetrating peptide is linked to the C-terminus of the peptide either directly or indirectly via a linker.

In specific embodiments of the present invention, there is provided a peptide-derived inhibitor comprising the sequence set forth in the table below:

KDM5C peptide inhibitor sequence complete with delivery peptide.

| Inhibitor | Sequence |
|---|---|
| EP4-TAT | TEDSKTHHH(SEQ ID NO: 4){6-aminohexanoic acid}GRKKRRQRRRPPQ(SEQ ID NO: 45) |
| EP4-PR9 | TEDSKTHHH(SEQ ID NO: 4){6-aminohexanoic acid} FFLIPKGRRRRRRRRR(SEQ ID NO: 49) |
| EP4-CPP | TEDSKTHHH(SEQ ID NO: 4){6-aminohexanoic acid}RRWRRWRRWRR(SEQ ID NO: 50) |

The peptides of the present invention can be biochemically synthesized such as by using standard solid phase techniques. These methods include exclusive solid phase synthesis, partial solid phase synthesis methods, fragment condensation, classical solution synthesis. Solid phase polypeptide synthesis procedures are well known in the art.

Recombinant techniques may also be used to generate the peptides of the present invention. Such recombinant techniques are known in the art. Accordingly, the present invention also provides a nucleic acid encoding the amino acid sequence of the peptide, and conjugates comprising the peptide. The nucleic acid can comprise DNA or RNA, and can be single or double stranded. Furthermore, the nucleic acid can comprise nucleotide analogues or derivatives (e.g. inosine or phophorothioate nucleotides and the like). The nucleic acid can encode the amino acid sequence of the peptide as part of a fusion protein comprising such sequence and a cell penetrating motif. The nucleic acid encoding the amino acid sequence of the peptide can be provided as part of a construct comprising the nucleic acid and elements that enable delivery of the nucleic acid to a cell, and/or expression of the nucleic acid in a cell. Such elements include, for example, expression vectors and transcription and/or translation sequences. Suitable vectors, transcription/translation sequences, and other elements, as well as methods of preparing such nucleic acids and constructs, are known in the art.

Accordingly, in certain embodiments polynucleotide encoding and expressing one or more peptide(s) of the invention. In another preferred embodiment, the polynucleotide is inserted in a vector. Preferably, said recombinant vector is an expression vector capable of expressing said polynucleotide when transfected or transformed into a host cell such as a prokaryotic or eukaryotic cell. The polynucleotide is inserted into an expression vector in proper orientation and correct reading frame for expression. In certain embodiments, the polynucleotide is operably linked to at least one transcriptional regulatory sequence and, optionally to at least one translational regulatory sequence. Recombinant vectors are known in the art and include but are not limited to plasmids and viral vectors. Viral vectors include but are not limited to oncolytic viral vectors, lentivirus and adenovirus vectors.

Pharmaceutical Compositions:

The peptides and peptide derived inhibitors of the present invention be formulated as a pharmaceutical composition. In certain embodiments, the pharmaceutical composition comprises one or more peptides and peptide derived inhibitors of the invention alone or in combination with one or more other active agents and a pharmaceutically acceptable carrier.

Polynucleotides and vectors encoding the peptides of the invention may also be formulated as pharmaceutical compositions. In certain embodiments, the pharmaceutical composition comprises one or more polynucleotides or one or more vectors of the present invention alone or in combination with one or more other active agents and a pharmaceutically acceptable carrier.

The pharmaceutical composition may comprise one or more other pharmaceutically active agents or drugs. Examples of such other pharmaceutically active agents or drugs that may be suitable for use in the pharmaceutical composition include anticancer agents. Suitable anticancer agents include, without limitation, alkylating agents; nitrogen mustards; folate antagonists; purine antagonists; pyrimidine antagoinists; spindle poisons; topoisomerase inhibitors; apoptosis inducing agents; angiogenesis inhibitors; podophyllotoxins; nitrosoureas; cisplatin; carboplatin; interferon; asparginase; tamoxifen; leuprolide; flutamide; megestrol; mitomycin; bleomycin; doxorubicin; irinotecan; and taxol, geldanamycin and various anti-cancer peptides and antibodies.

The carrier may be any of those conventionally used and is limited only by physio-chemical considerations, such as solubility and lack of reactivity with the active compound(s), and by the route of administration. The pharmaceutically acceptable carriers described herein, for example, vehicles, adjuvants, excipients, and diluents, are well-known to those skilled in the art and are readily available to the public. The pharmaceutically acceptable carrier may be one which is chemically inert to the active agent(s) and one which has no detrimental side effects or toxicity under the conditions of use.

The choice of carrier will be determined in part by the active agents, as well as the method of administration. Accordingly, there are a variety of suitable formulations of the pharmaceutical composition of the present inventive methods. The following formulations for oral, aerosol, topical, parenteral, subcutaneous, intravenous, intramuscular, interperitoneal, rectal, and vaginal administration are exemplary and are in no way limiting. One skilled in the art will appreciate that these routes of administering the compound of the invention are known, and, formulations appropriate for each of these routes of administration are known in the art.

In certain embodiments, one or more peptides of the present invention are conjugated, directly or indirectly, to a carrier. Appropriate carriers are known in the art and include but are not limited to proteins including but not limited to keyhole limpet hemocyanin (KLH), bovine serum albumin (BSA) and ovalbumin (OVA); virus-like particles and viruses.

Methods of Treatment

The present invention also provides methods of inhibiting KDM5C activity. This method comprises bringing KDM5C into contact with a peptide, peptide derived inhibitor or a pharmaceutical composition of the present invention. This contact may occur in vivo or in vitro. Accordingly, in certain embodiments, the present invention provides methods of inhibiting the activity of KDM5C in a subject in need thereof, by administering one or more peptide(s), one or more peptide(s) derived inhibitor(s), one or more polynucleotide(s) or vector(s) encoding one or more peptide(s) or one or more pharmaceutical composition(s) of the present invention alone or in combination with one or more other active agents. The subject may be a mammal. In certain embodiments, the subject is a human.

The present invention also provides methods of treatment of disease associated with increased KDM5C activity. Accordingly, in certain embodiments, the present invention provides methods of treatment of disease associated with increased KDM5C activity in a subject in need thereof, by administering to the with one or more peptide(s), one or more peptide(s) derived inhibitor(s), one or more polynucleotide(s) or vector(s) encoding one or more peptide(s) or one or more pharmaceutical composition(s) of the present invention alone or in combination with one or more other active agents.

In certain embodiments, the disease associated with increased KDM5C activity is a proliferative disease. In certain embodiments, the proliferative disease is cancer. Accordingly, in certain embodiments, the present invention provides methods of treatment of a cancer associated with increased KDM5C activity in a subject in need thereof, by administering one or more peptide(s), one or more peptide(s) derived inhibitor(s), one or more polynucleotide(s) or vector(s) encoding one or more peptide(s) or one or more pharmaceutical composition(s) of the present invention alone or in combination with one or more other active agents.

The types of cancer include but are not limited to a cancer selected from the group consisting of acoustic neuroma; adenocarcinoma; adrenal gland cancer; anal cancer; angiosarcoma (e.g. lymphangiosarcoma, lymphangioendothelio sarcoma, hemangio sarcoma); appendix cancer; benign monoclonal gammopathy; biliary cancer (e.g. cholangiocarcinoma); bladder cancer; breast cancer (e.g. adenocarcinoma of the breast, papillary carcinoma of the breast, mammary cancer, medullary carcinoma of the breast, triple negative breast cancer (TNBC), ER positive breast cancer, ER negative breast cancer, PR positive breast cancer, PR negative breast cancer, ER/PR positive breast cancer, ER/PR negative breast cancer, HER2 positive breast cancer, HER2 negative breast cancer); brain cancer (e.g. meningioma, glioblastomas, glioma (e.g. astrocytoma, oligodendroglioma), medulloblastoma); bronchus cancer; carcinoid tumor; cervical cancer (e.g. cervical adenocarcinoma, squamous cell carcinoma of the cervix); choriocarcinoma; chordoma; craniopharyngioma; colorectal cancer (e.g. colon cancer, rectal cancer, colorectal adenocarcinoma); connective tissue cancer; epithelial carcinoma; ependymoma; endotheliosarcoma (e.g. Kaposi's sarcoma, multiple idiopathic hemorrhagic sarcoma); endometrial cancer (e.g. uterine cancer, uterine sarcoma); esophageal cancer (e.g. adenocarcinoma of the esophagus, Barrett's adenocarcinoma); Ewing's sarcoma; ocular cancer (e.g. intraocular melanoma, retinoblastoma); familiar hypereosinophilia; gall bladder cancer; gastric cancer (e.g. stomach adenocarcinoma); gastrointestinal stromal tumor (GIST); germ cell cancer; head and neck cancer (e.g. head and neck squamous cell carcinoma, oral cancer (e.g. oral squamous cell carcinoma), throat cancer (e.g. laryngeal cancer, pharyngeal cancer, nasopharyngeal cancer, oropharyngeal cancer)); heavy chain disease (e.g. alpha chain disease, gamma chain disease, mu chain disease; hemangioblastoma; hypopharynx cancer;

inflammatory myofibroblastic tumors; immunocytic amyloidosis; kidney cancer (e.g. nephroblastoma a.k.a. Wilms' tumor, renal cell carcinoma); liver cancer (e.g. hepatocellular cancer (HCC), malignant hepatoma); lung cancer (e.g. bronchogenic carcinoma, small cell lung cancer (SCLC), non-small cell lung cancer (NSCLC), adenocarcinoma of the lung); leiomyosarcoma (LMS); mastocytosis (e.g. systemic mastocytosis); muscle cancer; myelodysplasia syndrome (MDS); mesothelioma; myeloproliferative disorder (MPD) (e.g. polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g. neurofibromatosis (NF) type 1 or type 2, schwannomatosis); neuroendocrine cancer (e.g. gastroenteropancreatic neuroendocrine tumor (GEP-NET), carcinoid tumor); osteosarcoma (e.g. bone cancer); ovarian cancer (e.g. cystadenocarcinoma, ovarian embryonal carcinoma, ovarian adenocarcinoma); papillary adenocarcinoma; pancreatic cancer (e.g. pancreatic andenocarcinoma, intraductal papillary mucinous neoplasm (IPMN), Islet cell tumors); penile cancer (e.g. Paget's disease of the penis and scrotum); pinealoma; primitive neuroectodermal tumor (PNT); plasma cell neoplasia; paraneoplastic syndromes; intraepithelial neoplasms; prostate cancer (e.g. prostate adenocarcinoma); rectal cancer; rhabdomyosarcoma; salivary gland cancer; skin cancer (e.g. squamous cell carcinoma (SCC), keratoacanthoma (KA), melanoma, basal cell carcinoma (BCC)); small bowel cancer (e.g. appendix cancer); soft tissue sarcoma (e.g. malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g. seminoma, testicular embryonal carcinoma); thyroid cancer (e.g. papillary carcinoma of the thyroid, papillary thyroid carcinoma (PTC), medullary thyroid cancer); urethral cancer; vaginal cancer; and vulvar cancer (e.g. Paget's disease of the vulva).

In specific embodiments of the present invention, there is provided a method of treatment of a cancer in a subject in need thereof, by administering to the with a peptide, peptide derived inhibitor or a pharmaceutical composition of the present invention, wherein the cancer is selected from the group consisting of bladder, non-small lung carcinoma, small cell lung carcinoma, leukemia, liver, breast, colon, and pancreatic cancer.

In certain embodiments, the cancer is a metastatic cancer.

In certain embodiments, one or more peptide(s), one or more peptide(s) derived inhibitor(s), one or more polynucleotide(s) or vector(s) encoding one or more peptide(s) or one or more pharmaceutical composition(s) of the present invention are used in combination with additional pharmaceutical agents in the methods of the present invention.

The additional pharmaceutical agents may include but are not limited to anti-cancer agents. Anti-cancer agents encompass biotherapeutic anti-cancer agents as well as chemotherapeutic agents.

Exemplary biotherapeutic anti-cancer agents include, but are not limited to, interferons, cytokines (e.g. tumor necrosis factor, interferon a, interferon γ), vaccines, hematopoietic growth factors, monoclonal serotherapy, immuno stimulants and/or immunodulatory agents (e.g. IL-1, 2, 4, 6, or 12), immune cell growth factors (e.g. GM-CSF) and antibodies (e.g. HERCEPTIN (trastuzumab), T-DM1, AVASTIN (bevacizumab), ERBITUX (cetuximab), VECTIBIX (panitumumab), RITUXAN (rituximab), BEXXAR (tositumomab)).

Exemplary chemotherapeutic agents include, but are not limited to, anti-estrogens (e.g. tamoxifen, raloxifene, and megestrol), LHRH agonists (e.g. goscrclin and leuprolide), anti-androgens (e.g. flutamide and bicalutamide), photodynamic therapies (e.g. vertoporfin (BPD-MA), phthalocyanine, photo sensitizer Pc4, and demethoxy-hypocrellin A (2BA-2-DMHA)), nitrogen mustards (e.g. cyclophosphamide, ifosfamide, trofosfamide, chlorambucil, estramustine, and melphalan), nitrosoureas (e.g. carmustine (BCNU) and lomustine (CCNU)), alkylsulphonates (e.g. busulfan and treosulfan), triazenes (e.g. dacarbazine, temozolomide), platinum containing compounds (e.g. cisplatin, carboplatin, oxaliplatin), vinca alkaloids (e.g. vincristine, vinblastine, vindesine, and vinorelbine), taxoids (e.g. paclitaxel or a paclitaxel equivalent such as nanoparticle albumin-bound paclitaxel (Abraxane), docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated pro-drug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g. 2'-paclitaxel methyl 2-glucopyranosyl succinate; docetaxel, taxol), epipodophyllins (e.g. etoposide, etoposide phosphate, teniposide, topotecan, 9-aminocamptothecin, camptoirinotecan, irinotecan, crisnatol, mytomycin C), antimetabolites, DHFR inhibitors (e.g. methotrexate, dichloromethotrexate, trimetrexate, edatrexate), IMP dehydrogenase inhibitors (e.g. mycophenolic acid, tiazofurin, ribavirin, and EICAR), ribonuclotide reductase inhibitors (e.g. hydroxyurea and deferoxamine), uracil analogs (e.g. 5-fluorouracil (5-FU), floxuridine, doxifluridine, ratitrexed, tegafur-uracil, capecitabine), cytosine analogs (e.g. cytarabine (ara C), cytosine arabinoside, and fludarabine), purine analogs (e.g. mercaptopurine and Thioguanine), Vitamin D3 analogs (e.g. EB 1089, CB 1093, and KH 1060), isoprenylation inhibitors (e.g. lovastatin), dopaminergic neurotoxins (e.g. I-methyl-4-phenylpyridinium ion), cell cycle inhibitors (e.g. staurosporine), actinomycin (e.g. actinomycin D, dactinomycin), bleomycin (e.g. bleomycin A2, bleomycin B2, peplomycin), anthracycline (e.g. daunorubicin, doxorubicin, pegylated liposomal doxorubicin, idarubicin, epirubicin, pirarubicin, zorubicin, mitoxantrone), MDR inhibitors (e.g. verapamil), Ca<2+> ATPase inhibitors (e.g. thapsigargin), imatinib, thalidomide, lenalidomide, tyrosine kinase inhibitors (e.g. axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTEVIA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TK1258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ- 26483327, MGCD265, DCC-2036, BMS-690154, CEP-11981, tivozanib (AV-951), OSI-930, MM-121, XL-184, XL-647, and/or XL228), proteasome inhibitors (e.g. bortezomib (VELCADE)), mTOR inhibitors (e.g. rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, caraiinomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin,, aminopterin, and hexamethyl melamine.

EXAMPLE

The example below details the development of peptide inhibitors that target KDM5C. The focus on the KDM5 family (histone H3K4me2/3 demethylases) results from growing evidence for a causal role of these KDMs in a number of different human cancers, contributing to cancer cell proliferation and drug resistance. KDM5C in ovarian, breast, prostate, and colon cancer, in addition to other tumors, is highly expressed and involved in the regulation of tumor-related gene expression through the abnormal demethylation of histone H3K4me2/3. Colon cancer is the second most common among malignant solid tumors. Chemotherapy is a standard treatment for this disease; however, the number of effective chemotherapy drugs available to treat colon cancer is limited. Recent studies have shown that KDM5C may have a specific role in drug resistance in colon cancer, and that KDM5C is overexpressed in some lung, gastric and cervical cancers (Lin et al., 2018). The importance of KDM5 H3K4me2/3-specific demethylase activity towards its role in cell proliferation and drug resistance in cancer has not been resolved so far, and it's unclear how much of KDM5's role in cancer is attributable to histone-specific demethylation. KDM5C regulation is extensive and has been reported to downregulate the genes that regulate cell proliferation, including the tumor protein p53, PCNA, MK167, and the cyclin-dependent inhibitor, p21, thereby promoting cell proliferation (Xu et al., 2017; Stein et al., 2014). In agreement with these findings, unpublished preliminary research from the Biggar lab also suggests that KDM5C may also function through the demethylation of the tumor protein, p53 at trimethylated lysine K370me3, effectively decreasing p53 activity and decreasing the expression of p21 and PCNA. Furthermore, KDM5C downregulates BMP7 in liver cancer and BRMS1 in breast cancer to promote invasion, inhibits the von-Hippel Lindau (VHL) tumor suppressor gene, and has been shown to downregulate ABCC1 expression thereby promoting drug resistance in colon cancer (Lin et al., 2018; Stein et al, 2014; Ji et al., 2015; Wang et al., 2015). Interestingly, this presents a mechanism whereby KDM5C inhibition may decrease drug cancer cell resistance in colon cancer, but may also be a conserved mechanism for the treatment of other KDM5C-dependent cancers. As a result of its established role in cancer development and progression, there has been significant interest in the development of KDM5-specific inhibitors. To date, one highly regarded inhibitor of the KDM5 family of demethylases is available under the name CPI-455 and has been shown to increase global H3K4me3 methylation levels, however, this inhibitor unfortunately has weak activity towards KDM5 inhibition in vivo with an IC50 of ~25 uM (Vinogradova et al., 2016).

Materials and Methods

KDM5C Construct Information

The plasmid used to product recombinant KDM5C was:

Vector Name: pFB-CT10HF-LIC

Construct ID: JARID1CA-c022

The sequence of recombinant KDM5C is set forth below (SEQ ID NO:64):

```
MEPGSDDFLPPPECPVFEPSWAEFRDPLGYIAKIRPIAEKSGICKIRPP
ADWQPPFAVEVDNFRFTPRIQRLNELEAQTRVKLNYLDQIAKFWEIQGS
SLKIPNVERRILDLYSLSKIVVEEGGYEAICKDRRWARVAQRLNYPPGK
NIGSLLRSHYERIVYPYEMYQSGANLVQCNTRPFDNEEKDKEYKPHSIP
LRQSVQPSKFNSYGRRAKRLQPDPEPTEEDIEKNPELKKLQIYGAGPKM
MGLGLMAKDKTLRKKDKEGPECPPTVVVKEELGGDVKVESTSPKTFLES
KEELSHSPEPCTKMTMRLRRNHSNAQFIESYVCRMCSRGDEDDKLLLCD
GCDDNYHIFCLLPPLPEIPKGVWRCPKCVMAECKRPPEAFGFEQATREY
TLQSFGEMADSFKADYFNMPVHMVPTELVEKEFWRLVNSIEEDVTVEYG
ADIHSKEFGSGFPVSDSKRHLTPEEEEYATSGWNLNVMPVLEQSVLCHI
NADISGMKVPWLYVGMVFSAFCWHIEDHWSYSINYLHWGEPKTWYGVPS
LAAEHLEEVMKKLTPELFDSQPDLLHQLVTLMNPNTLMSHGVPVVRTNQ
CAGEFVITFPRAYHSGFNQGYNFAEAVNFCTADWLPAGRQCIEHYRRLR
RYCVFSHEELICKMAACPEKLDLNLAAAVHKEMFIMVQEERRLRKALLE
KGITEAEREAFELLPDDERQCIKCKTTCFLSALACYDCPDGLVCLSHIN
DLCKCSSSRQYLRYRYTLDELPAMLHKLKV
```

Purification of Recombinant Target Proteins

Expression and Purification of KDM5C

SF9 cells (500 mL at $10^6$ cells/mL) were infected with KDM5C-$His_6$ baculovirus at a 1:100 ratio. After 60 hr post-infection, cells were harvested by centrifugation and the pellet was frozen on liquid nitrogen. Cells were lysed in P5 buffer (50 mM NaHPO4 pH 7, 500 mM NaCl, 10% glycerol, 0.05% TritonX-100, 0.5 mM DTT, 5 mM Imidazole and protease inhibitors) and homogenized by 20 passes through a dounce homogenizer (pestle A) followed by sonication (three times each for 30 sec at 40% intensity). The dounce homogenized cell lysate was incubated with 1 mM $MgCl_2$ and 2.5 U/ml benzonase nuclease at 4° C. for 1 hr followed by centrifugation at 18,000 g for 45 min. The soluble cell lysate was incubated with prewashed 200 μL HisPur™ Ni-NTA Resin with P5 buffer for 1 hr at 4° C. The beads were pelleted by centrifugation at 800×g for 2 min, the supernatant was removed and the beads were washed 4 times each of 5 min with P40 buffer under rotation at 4° C. Finally, the protein was eluted with P500 buffer. The purified protein was dialyzed in storage buffer (20 mM HEPES pH 7.5, 150 mM NaCl, 10% glycerol, 1 mM DTT), snap frozen on liquid nitrogen and stored in small aliquots at −80° C.

Synthesis of Oriented Peptide Array Library (OPAL)

The peptide libraries were synthesized on cellulose membrane using the ResPep SL automatic peptide and SPOT array synthesizer (Intavis). An extra fine needle tip was used to achieve a density of 600 peptides per SPOT membrane (8×12 cm). The following oriented peptide library arrays were synthesized for binding dependent interactions:

AXXXX[Lys]XXXXA and AXXXX[nor-Leu]XXXXA; where X is a mixture of 19 amino acids (except Cys), and the brackets ([/]) encase the amino acids that were preferred by the protein of interest. To generate oriented peptide library pools, each degenerated position was scanned with any of the 19 amino acids (excluding Cys).

Target Protein Binding Assays

The OPAL was designed sequentially starting from the most degenerate to highly specific peptide against our target protein as described above. The potential inhibitor peptides were initially screened based on the binding affinity between the peptides and target proteins. All the steps were carried out at room temperature unless otherwise stated. The OPAL cellulose macro arrays are presoaked in 100% ethanol followed by 50% ethanol for 15 min with constant rocking. The membrane is then washed with distilled water three times each of 15 min. The processed membrane is first blocked with 5% nonfat dry milk in Tris buffered saline containing 0.05% Tween 20 (TBST) for 1 hr at room temperature. Finally, the array was equilibrated with peptide binding buffer (50 mM Tris-Cl, 350 mM NaCl, 10% glycerol, 0.5 mM DTT and 0.05% Tween20). The array was then incubated with 1 μM of target protein overnight at 4° C. under rotation. The excess protein was washed away by three consecutive 10 min washes with TBST. Each array was then incubated with HRP conjugated anti-His antibody (1:5000) in TBST for 1 hr. The array was then washed thrice each of 10 min. The signals were detected using chemiluminescence. The signal intensities observed were subjected to densitometry analysis using ImageJ software protein array analyzer.

In Vitro Lysine Demethylase Activity Inhibition Assay

Inhibition of in vitro demethylase activity by the peptides was analysed using Succinate-Glo™ JmjC demethylase assay kit (Promega). The experiment was performed in low-volume 384-well plates at room temperature as per the manufacturer's instruction.

Fluorescent Polarization

Recombinant KDM5C protein was serially diluted in a 384-well plate, followed by the addition of fluorescein-labeled inhibitor peptide in PBS buffer. The mixtures were incubated in the dark for 30 min prior to fluorescent polarization measurements at room temperature on an EnVision Multilabel Plate Reader (PerkinElmer) with the excitation set at 480 nm and emission at 535 nm. Binding curves were generated by fitting the binding data to a hyperbolic non-linear regression model using Prism 3.0 (GraphPad software, Inc., San Diego, CA), which also produced the corresponding dissociation constants ($K_d$).

Delivery of Inhibitor Peptide to the Cell Line

Synthesis of three different cell penetrating peptide with sequence Gly-Arg-Lys-Lys-Arg-Arg-Gln-Arg-Arg-Arg-Pro-Pro-Gln (i.e., TAT (SEQ ID NO:45)), Phe-Phe-Leu-Ile-Pro-Lys-Gly-(Arg)s (i.e., PR9 (SEQ ID NO:49)) and (Arg-Arg-Trp)$_3$-Arg-Arg (i.e., MutD6 or CPP (SEQ ID NO:50)) were carried out by solid phase synthesis on a ResPep SL peptide synthesizer (INTAVIS)) following the Fmoc chemistry protocol. A 6-carboxyfluorescein (FITC derivative, referred to as only FITC in this document) was added to the C-terminal end of the peptides for ligation to a fluorochrome FITC and was separated by the addition of a 6-amino-hexanoic acid group to provide both (1) fluor flexibility and (2) reduce steric constraints of the molecule.

To evaluate the internalization of FITC-labelled peptides, exponentially growing HCT 116 cells were seeded on 6 well plate at a density of $2\times10^5$ cells per well and incubated overnight. After overnight incubation, the media (DMEM with penstrep and 10% FBS) was replaced with fresh media supplemented with 10 μM FITC-labelled inhibitor peptides. Following the incubation (24 hr), cells were washed three times with ice cold PBS to remove the excess extracellular complexes. Cells were then stained with Hoechst dye (1:2000 dilution from 10 mg/mL stock in PBS) directly adding sufficient staining solution to the well. Cells were incubated for 10 min with the dye, protected from light. The staining solution is discarded and the cells were washed 3 times with PBS and imaged directly under fluorescent microscope.

Cell Viability Assay and $IC_{50}$ Determination

Cell viability was measured using the Resazurin reduction assay which indirectly quantifies living cells through the metabolically active reduction of resazurin to fluorescent resorufin. This assay allows to maintain cells viability and, therefore, to monitor cell growth with time. Exponentially growing cells were seeded into 96-well plates at the density of $2.0\times10^4$ cells/mL and incubated overnight. The media was replaced with fresh media prior to inhibitor treatment. Cells were treated with 0.2 μM of inhibitor peptide for 24 hr. The inhibitor peptide was diluted in the cell culture media (DMEM –/–) in the absence of serum from a 5 mM stock. All the treated cells were compared to the control (TAT alone peptide with equivalent quantity of DMSO) which were considered as 100% viable. One set of wells also prepared with medium only for background subtracting and instrument gain adjustment. The experiments were carried out in triplicate and expressed as mean±SD. A 10% resazurin solution (0.15 mg/ml stock dissolved in PBS, filter sterilized and stored protected from light at 4° C.) was then added to each well and incubated for 2 hr. The fluorescence was recorded using a multiwell plate reader (Perkin Elmer) at Ex. 560 nm and Em. 610 nm.

Inhibition of Target Enzyme Activity in HCT 116 Cell Line

The EP4-TAT inhibitor from all the above experiments were tested for histone methylation status in HCT 116 cells. $3\times10^6$ cells were plated in 10 cm dish and incubated overnight. Cells were then treated with the inhibitors at various concentrations (0.001 to 15 μM). Cells ($5\times10^6$ cells/mL), 24 hr of post dosing, were collected in 15 mL falcon tube and centrifuged at 300×g for 10 min. The supernatant was discarded and the cells are washed with iced cold PBS. The cell pellet is flash-frozen in liquid nitrogen and stored at −80° C. Histone isolation is done using standard protocol. To summarize, cells were re-suspended in 1 mL hypotonic lysis buffer (10 mM Tris-HCl pH 8, 1 mM KCl, 1.5 mM $MgCl_2$ and 1 mM DTT) containing protease inhibitor. The cells were transferred to 1.5 mL tube and incubated for 30 min on rotor at 4° C. to promote hypotonic swelling and lysis. The intact nuclei are collected by centrifugation at 10,000×g for 10 min in a cooled tabletop centrifuge. The supernatant is entirely discarded and pellets were re-suspended completely in 600 μL 0.4N $H_2SO_4$ and incubated overnight on rotor at 4° C. The nuclear debris were removed by centrifugation at 16,000×g for 10 min. The supernatant containing the histones were transferred to a fresh 1.5 mL tube and precipitated by adding 195 μL TCA (33%) drop by drop. The reaction is incubated at 4° C. overnight under rotation. The histones were pelleted by centrifugation at 16,000×g for 10 min. After complete removal of the supernatant carefully, the histone pellets were washed with ice-cold acetone to remove the left-over acids without disturbing the pellet. Finally, the pellets were air dried for 30 min at room temperature. The histone pellets were dissolved in 100 μL milliQ water and stored frozen at −20° C. Samples of 1, 3 and 5 μL of histones were separated on 15% SDS-PAGE gel and stained with Coomassie Brilliant Blue and characterized on the quality and concentration of the histone. The locations of the linker histone H1 and the core histones H3, H2B, H2A and H4 were noted.

For western blot, of total of 1 μL of histones were separated on 15% SDS-PAGE and transferred overnight at 15V on PVDF membrane. Following blocking with 5% nonfat dry milk in 1×TBST for 1 hr, the membrane containing histones lanes treated with inhibitor, were probed with H3K4Me3 (Abcam) primary antibody (1:2500) in 1×PBST. Both the membranes were incubated overnight at 4° C. under rotation. Following this incubation, membranes were washed in 1×TBST and 1×PBST respectively for 30 min, followed by incubation with secondary antibody for an additional 1 hr. The membranes were further washed for 30 min as before. Histone proteins were detected by Supersignal™ West Pico PLUS Chemiluminescent substrate (ThermoFisher Scientific) using the Chemidoc XRS+ imaging system (BioRad).

Flow Cytometry

A total of $0.3\times10^6$ HCT 116 cells were plated in 6 well-plate and incubated overnight. Cells were treated with the inhibitor, DMSO and TAT alone controls. For each condition, approximately $1\times10^6$ HCT 116 cells were collected along with the floating cells in the media by centrifugation at 300×g for 10 min. The cells were then washed with 5 mL of ice-cold PBS and re-suspended in 0.5 mL of ice-cold PBS. The cells were slowly dropped into 4.5 mL of vortexing ice-cold 70% ethanol for rapid dispersion. The sample was incubated on ice for 45 min and then fixed at −20° C. overnight. The fixed cells were centrifuged at 4° C. at 300×g for 10 min. The resultant cell pellet was re-suspended to 200 μL of the stain master mix (133.7 μL of 1 mg/mL propidium iodide (PI), 1 μL of 10 mg/mL RNase A and PBS 865.3 μL). The PI-treated cells were incubated at 37° C. for 30 min and then analyzed by a flow cytometry (BD Accuri™ C6 Plus). The BD Accuri C6 Plus software version FCS 3.1 was used for apoptosis and cell cycle analysis.

NCI60 Cancer Cell Screen

Following the receipt at the NCI, cell-active EP4-TAT was be tested for its effects on cell viability in a dose-responsive manner in the complete panel. The effect of EP4-TAT on cell viability was carried out using Sulforhodamine B (SRB) staining in all 60 cell lines (n=4). Using several measurements [time zero ($T_z$), control growth (C), and growth at the five inhibitor concentrations ($T_i$)], the percentage growth will be calculated at each inhibition concentration. Three dose-response parameters are calculated: (1) $GI_{50}$ (drug concentration resulting in a 50% reduction in the net protein increase, $[(T_i-T_z)/(C-T_z)]\times100=50$), (2) TGI (drug concentration resulting in total growth inhibition, $T_i=T_z$), and (3) $LC_{50}$ ($[(T_i-T_z)/T_z]\times100=-50$).

Experimental Results

Identification of Potent High Affinity Target Binding Peptides

A high affinity peptide screen was carried out against target protein KDM5C. The method involves the sequential synthesis and printing of OPALs. FIG. 1 shows the binding of KDM5C to the unselective degenerate peptide arrays. The intensity of dark spots represents the binding affinity which is quantified by ImageJ protein array analyzer.

Further the best hits from the arrays were then used to design sequence-selective peptides followed next by the sequence-specific high affinity peptides. At the end of the experiment, 44 KDM5C specific potential high affinity peptides were selected.

In Vitro Validation: KDMase Inhibition

Figure 2:
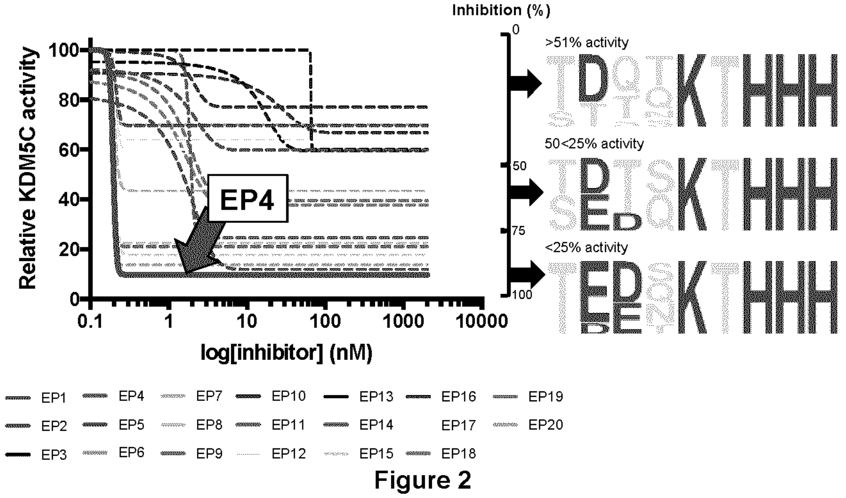
FIG. 2. Inhibition of in vitro KDM5C H3K4Me3 demethylase activity. Average ±SEM are shown (n=3, biological).

All the potential KDM5C inhibitors selected from the OPAL screen were tested for inhibition of KDM5C demethylation activity in vitro. KDM5C demethylation activity was carried out using a H3K4me3 substrate peptide. A total of 20 (EP1-EP20) inhibitor peptides, representing all lysine-derived versions of top inhibitor candidates from the OPAL screen, were tested for inhibitory activity in a dose-responsive manner (FIG. 2). EP4 was selected from this screen as it displayed the top-most inhibitory activity in vitro.

Figure 3:
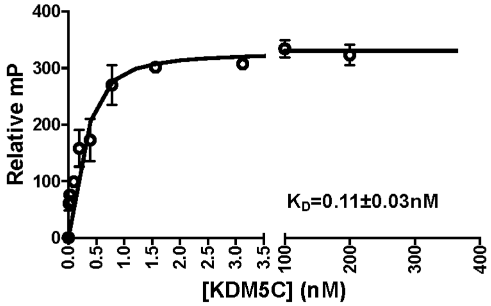
FIG. 3. Peptide inhibitor, EP4, dissociation constant with KDM5C. Interaction between EP4 and KDM5C binding analyzed by fluorescent polarization. The equilibrium dissociation constant ($K_D$) was obtained for the complex.

In order to quantify the dissociation kinetics of EP4 with KDM5C, fluorescent polarization was performed, and it was determined that EP4 bound to KDM5C with an experimental Kd of 0.11+/−0.03 nM (FIG. 3). EP4 was further shown to display in vitro specificity towards the inhibition of KDM5C activity in a panel of KDM5 paralogs (FIG. 4).

Characterization of Critical Binding Residues of EP4

Figure 5:
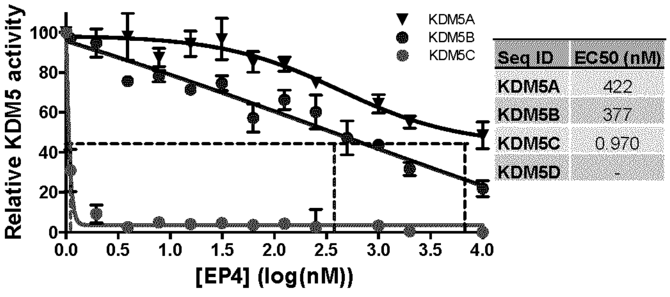
FIG. 5. In vitro target specificity of EP4 peptide within the KDM5 family. Relative recombinant KDM5 demethylation activity (KDM5A/B/C) towards H3K4me3 peptide in the presence of EP4 peptide. Data are averages+/−SEM (n=6 independent replicates). IC50 are reported as the [EP4] required to decrease KDM activity to 50% of control (i.e., no EP4) values.

The position and contribution of critical residues within the EP4 inhibitor were assessed by peptide array and in vitro recombinant KDM5C binding assay. Progressive C-terminal and N-terminal tandem truncations of EP4 sequence were used to assess the individual residue contribution of EP4 to KDM5C binding. Relative binding was qualitatively determined by chemiluminescence (FIG. 5; left). A systematic mutation of the EP4 was also carried out to in order to assess possible amino acid mutations that alter in vitro KDM5C binding activity, either resulting in a maintenance or strengthening (green; greater than 100%(relative EP4 binding)), tolerable (yellow; 80% percentile) or intolerable interaction (red; 50% percentile) (FIG. 5; right). The position-specific tolerable mutations that can be made to EP4 were determined by those amino acid substitutions that retained at least 100% of WT EP4 relative binding activity.

EP4 Peptide Interacts with the KDM5C Catalytic Domain

Figure 6:
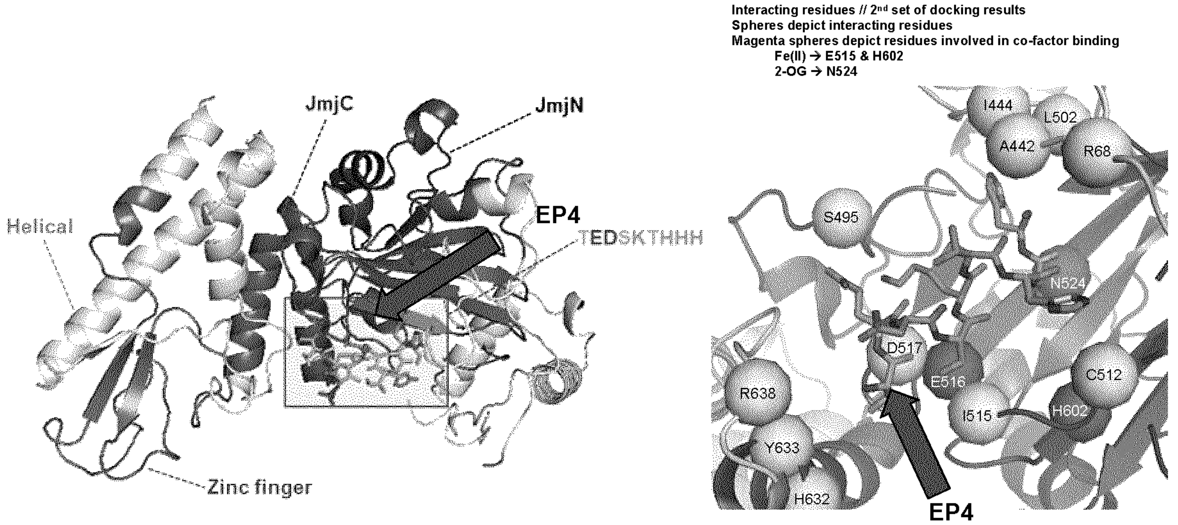
FIG. 6. Interaction with EP4 peptide with target KDM5C protein. The EP4 peptide was found to interact with the region of KDM5C that is responsible for cellular demethylation activity. These findings support biochemical data demonstrating that the EP4 can inhibit the demethylation activity of KDM5C and demonstrates that this inhibition occurs as a result of interaction with the KDM5C JmjC domain.

KDM5C quaternary structure, comprising the JmjN, JmjC and ZF domains, was modelled for predicting different binding sites using refined protein structure to identify spatial properties, backbone positioning, and protein-side-chain conformation that concurrently strengthens global topologies and protein modeling structural properties. Our structural model with the lowest score had a 0.110 RMSD (A). Each side-chain residue was created using the most plausible rotamer from the Dunbrack backbone-dependent rotamer library from UCSF Chimera. Auto-optimization for EP4 peptide is conducted with Avogadro to monitor poor contacts and improper bonds. For initial modelling of KDM5CA-EP4 complex, the inhibitor positing should substitute other co-factors in the investigational framework. This was achieved by superimposing template structure on the KDM5C catalytic core structure to replace template cofactors with other enzymatic cofactors. FIG. 6 shows the superimposed structure of the catalytic core KDM5C bound with inhibitor peptide. Different binding motifs were analyzed within KDM5C-A for predicting binding pocket for EP4 using Autodock 4 that employs Mozyme function of MOPAC2009 enabling fast, semi-empirical quantum mechanical calculation of the protein charge.

By this method, 200 clustered KDM5CA-EP4 protein peptide complex structures are synthesized and the top structure with the lowest z-score of −1.6 is predicted to yield the best possible binding interaction for EP4 peptide with KDM5C (FIG. 6). Further analyzation of the complex using Discovery studio visualizer detected the formation of salt bridges between the protein-peptide complex possessing heavy attractive charge and providing high stability within the complex. We also investigated 2D and 3D structural modelling of standard and mutated EP4 Inhibitory peptide sequences, EP4-2/8, EP4-T1A/H9A, EP4-T1A, EP4-H9A that revealed less significant interactions with KDM5C as compared to standard EP4 peptide structure, suggesting that any single deletion or additional modifications to EP4 sequence disrupts the integrity of the protein-peptide complex, thereby weakening the interactions.

Inhibitors were Delivered and Reduced Colorectal Carcinoma Cell Viability

Figure 7:
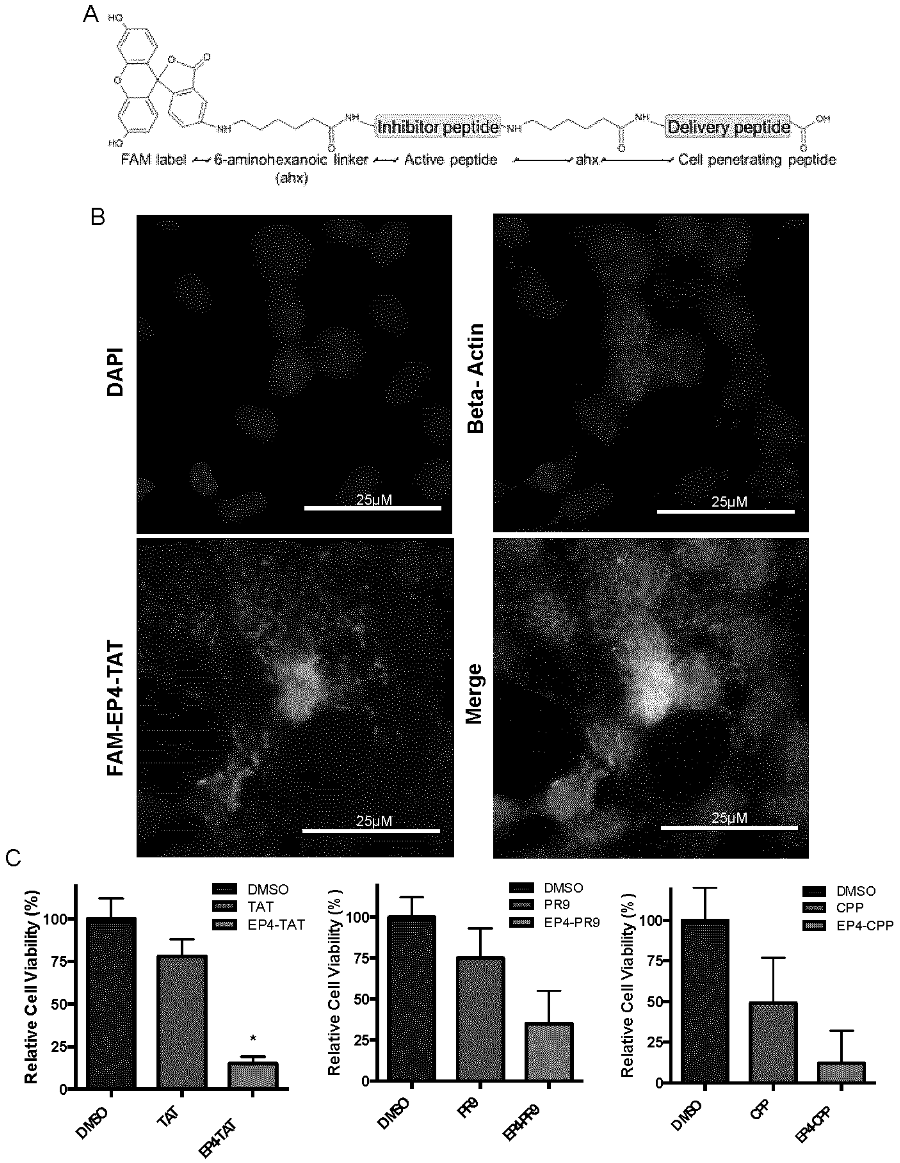
FIG. 7. Cellular EP4 inhibitor delivery and viability. (A) Diagrammatic representation of EP4 inhibitor peptide showing N-terminally tagged 6-carboxyfluorescein and C-terminally tagged TAT cell delivery peptide. (B) Immunofluorescence microscopy showing internalization of EP4-TAT peptide (shown in green) to HCT 116 cells imaged 24 hr post-treatment with inhibitor. (C) Cell viability following 10 μM treatment of EP4 peptide conjugated to cell penetrating peptides, TAT, PR9 and CPP.

Our EP4 KDM5C inhibitor peptide were tested for a decrease in cell viability. Individual peptide was tagged initially with 3 different cell penetrating peptide in order to decide the best cell delivery peptide (FIG. 7A). All the peptides were tagged with fluorophore FITC on the C terminal end. 10 μM of the FITC tagged peptides after 24 hr post treatment when visualized under the fluorescent microscope shown to be successfully delivered into the nucleus which is seen as green foci (FIG. 7B).

The cell penetrating peptide tagged EP4 inhibitors are then tested for loss of cell viability on colorectal carcinoma HCT 116 cell line at a 10 μM dose (FIG. 7C). EP4 peptide with a TAT tag showed maximum and consistent loss of cell viability. Cell penetrating peptide CPP by itself showed 50% loss of cell viability, followed by PR9 (30% loss) whose overall performance was also low compared to the TAT-inhibitors and hence discontinued further.

Flow Cytometry

Figure 8:
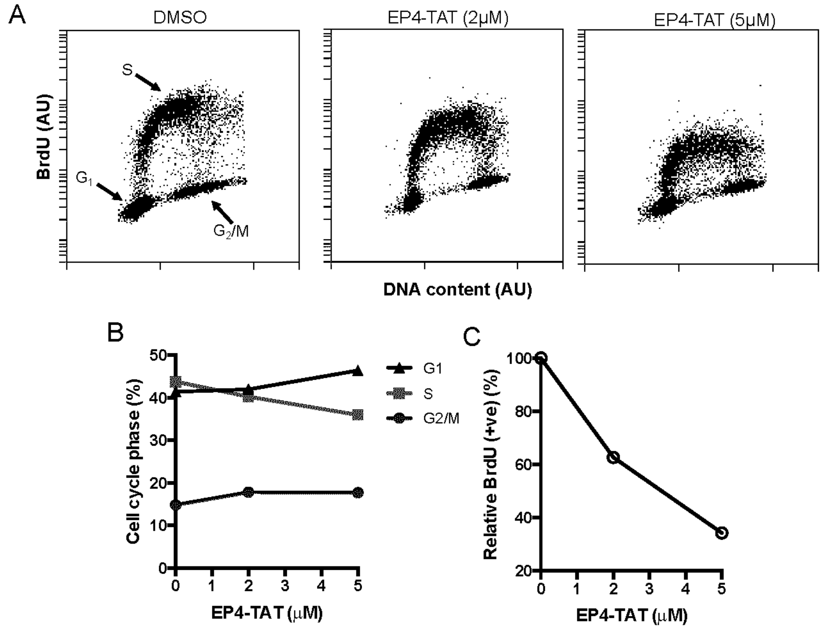
FIG. 8. Global cell cycle distribution in EP4-TAT treated HCT 116 cells. EP4-TAT increases global H3K4me3 levels in HCT 116 cells. (A) Two-parameter flow cytometric analysis of BrdU incorporation and DNA content was performed following a 24 hr exposure of 2 μM and 5 μM EP4-TAT to HCT 116 cells. (B) The proportion of propidium iodine stained cells were represented in each phase of the cell cycle cell cycle and (C) dose-response correlation of BrdU positive cells were represented. These values are expressed relative to untreated controls. Each value in B, C represents the mean (+/−SEM) determined from 3 independent experiments.

To determine whether loss in cell viability was associated with increased apoptosis, HCT 116 cells were treated with 2 μM of EP4-TAT and analyzed by PI staining. Representative data from flow cytometry analysis are shown in FIG. 8. Frequency distribution histogram shows an increasing percentage of subG1 peak in 2 μM EP4-TAT treated cells (52.8%) as compared to the untreated control (11.0%).

Figure 9:
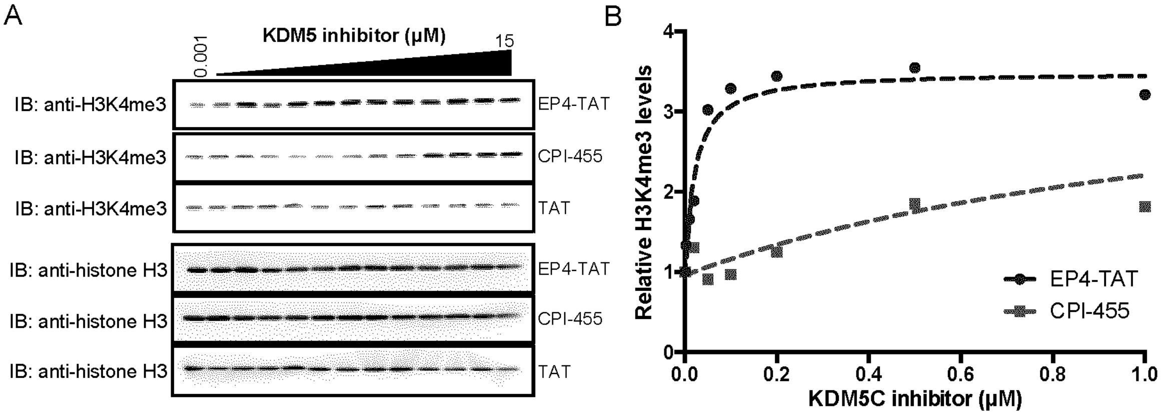
FIG. 9. Comparison of KDM5 inhibitors, EP4-TAT and CPI-455. (A) KDM5 inhibitors (EP4-TAT and CPI-455) increase global H3K4me3 levels in HCT 116 cells. (B) Relative H3K4me3 levels were monitored in histone extracts from HCT 116 cells.

Histone Lysine Methylation Status is Inhibitor-Responsive in Colorectal Carcinoma HCT 116 colorectal carcinoma cell line was treated with the KDM5C inhibitor EP4-TAT to test dynamic changes in H3K4 tri-methylation levels in comparison to the commercial KDM5 inhibitor, CPI-455. The demethylation of histone H3K4 tri-methylation was found to be inhibited when treated with 25 nM of the KDM5C inhibitor (FIG. 9A). EP4-TAT was deemed to be more effective for cellular KDM5C inhibition than that of the CPI-455 alternative (FIG. 9B).

EP4-TAT Performance on the NCI60 Cancer Panel Screen

Figure 10:
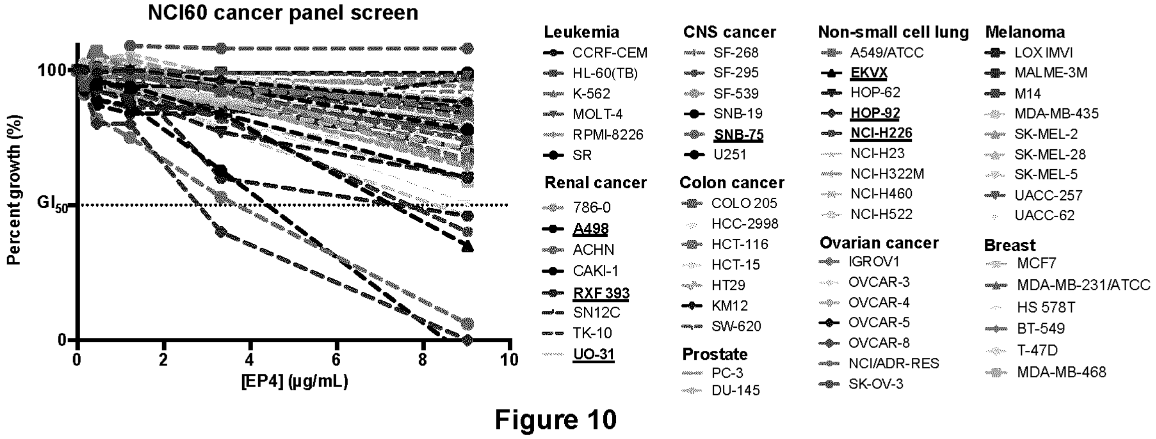
FIG. 10. NCI60 cancer panel screen of EP4-TAT. EP4-TAT and TAT-alone peptides were sent to the National Cancer Institute—Developmental Therapeutics program for screening effect on cell growth on the NCI60 cancer panel. Cell growth was monitored post-treatment with peptide in a dose-responsive manner (n=4). EP4-TAT effects were normalized to TAT-alone effects to control for delivery peptide. Following drug addition, the plates were incubated for an additional 48 hours at 37° C., 5% CO2, 95% air, and 100% relative humidity. Cell growth was monitored by Sulforhodamine B (SRB) staining. $GI_{50}$ values are defined at the concentration of EP4-TAT that decreased cell growth by 50%.

To determine the therapeutic breadth of our EP4-TAT peptide, we utilized the National Cancer Institute Developmental Therapeutics Program (NCI DTP) to screen EP4-TAT (vs. TAT alone) on a panel of 60 cancer cell lines (NCI60; representing leukemia, melanoma, and lung, colon, brain, ovary, breast, prostate, and kidney cancers). EP4-TAT was found to have a growth inhibitory ($GI_{50}$) effect in 7 lines, spanning CNS (SNB-75) and renal (A498, RXF393, UO-31), and non-small cell lung cancer (NSCLC; HOP-92, NCI-226, EKVX) (FIG. 10).

EP4-TAT Increases Chemo-Sensitivity in NSCLC Cells

Figure 11:
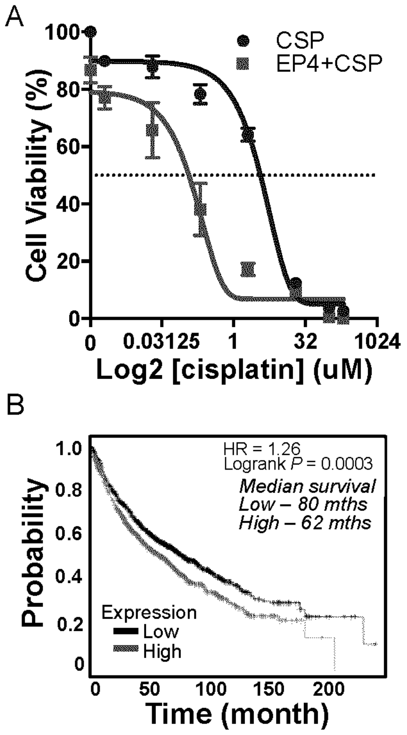
FIG. 11. EP4-TAT pre-treatment sensitizes non-small cell lung cancer cells to cisplatin treatment. (A) Non-small cell lung cancer cells (HOP-92) were exposed to 0.2 μM EP4-TAT peptide for 24 hr prior to a 72 hr dose-response treatment with cisplatin. Cell viability is determined by resazurin assay and is relative to a 0.2 μM TAT-alone control treatment. (B) Kaplan-Meier survival plot of KDM5C expression in NSCLC patients.

As KDM5C has also been reported to facilitate drug resistance, we explored the potential of EP4-TAT to increase sensitivity to chemotherapies. We have focused this study towards cisplatin treatment as KDM5C inhibition is reported to reduce resistance to platinum-based drugs ( ) and EP4-TAT responsive NCI60 cancers (FIG. 10) are generally cisplatin-responsive. Further, an EP4-TAT responsive NSCLC line (HOP-92) robustly displayed a decreased cisplatin $IC_{50}$ following pre-exposure to EP4-TAT (FIG. 11A). In patients of NSCLC, a higher KDM5C expression in is prognostic of a lower median survival (FIG. 11B).

Top KDM5C inhibitors screened from OPAL array.

| SEQ ID NO: | Experimental Peptide | Sequence |
|---|---|---|
| 1 | EP 1 | T D T T K T H H H |
| 2 | EP 2 | T D T Q K T H H H |
| 3 | EP 3 | T D T N K T H H H |
| 4 | EP 4 | T E D S K T H H H |
| 5 | EP 5 | T E D Q K T H H H |
| 6 | EP 6 | T T Q S K T H H H |
| 7 | EP 7 | T D T S K T H H H |
| 8 | EP 8 | T E D T K T H H H |
| 9 | EP 9 | T E E Q K T H H H |
| 10 | EP 10 | S D Q Q K T H H H |
| 11 | EP 11 | T T Q Q K T H H H |
| 12 | EP 12 | S D Q T K T H H H |
| 13 | EP 13 | T D D Q K T H H H |
| 14 | EP 14 | T E E N K T H H H |
| 15 | EP 15 | T E E S K T H H H |
| 16 | EP 16 | T T Q T K T H H H |
| 17 | EP 17 | T D S T K T H H H |
| 18 | EP 18 | S E T Q K T H H H |
| 19 | EP 19 | S E T S K T H H H |
| 20 | EP 20 | T D D N K T H H H |
| 21 | EP 21 | T D T T n T H H H |
| 22 | EP 22 | T D T Q n T H H H |
| 23 | EP 23 | T D T N n T H H H |
| 24 | EP 24 | T E D S n T H H H |
| 25 | EP 25 | T E D Q N T H H H |
| 26 | EP 26 | T T Q S n T H H H |
| 27 | EP 27 | T D T S n T H H H |
| 28 | EP 28 | T E D T n T H H H |
| 29 | EP 29 | T E E Q n T H H H |
| 30 | EP 30 | S D Q Q n T H H H |
| 31 | EP 31 | T T Q Q n T H H H |
| 32 | EP 32 | S D Q T n T H H H |
| 33 | EP 33 | T D D Q n T H H H |
| 34 | EP 34 | T E E N n T H H H |
| 35 | EP 35 | T E E S n T H H H |

-continued

| Top KDM5C inhibitors screened from OPAL array. | | |
|---|---|---|
| SEQ ID NO: | Experimental Peptide | Sequence |
| 36 | EP 36 | T T Q T n T H H H |
| 37 | EP 37 | T D S T n T H H H |
| 38 | EP 38 | S E T Q n T H H H |
| 39 | EP 39 | S E T S n T H H H |
| 40 | EP 40 | T D D N n T H H H |
| 41 | EP 41 | R T K Q T A R K S T G G |
| 42 | EP 42 | R T n Q T A R K S T G G |
| 43 | EP 43 | G A K R H R K V L R D N I |
| 44 | EP 44 | G A K R H R n V L R D N I |

REFERENCES

Arrowsmith C H, Bountra C, Fish P V, Lee K, Schapira M. Epigenetic protein families: a new frontier for drug discovery. Nat. Rev. Drug Discov. 2012; 11, 384-400.

Beck-Sickinger A G, Mörl K. Posttranslational Modification of Proteins. Expanding Nature's Inventory. By Christopher T. Walsh. Angew. Chem. Int. Ed. 2006; 45, 1020-1020.

Biggar K K, Li SSC. Non-histone protein methylation as a regulator of cellular signaling and function. Nat. Rev. Mol. Cell Biol. 2015; 16, 5-17.

Blum G, Ibanez G, Rao X, Shum D, Radu C, Djaballah H, et al. Small-molecule inhibitors of Set8 with cellular activity. ACS Chem. Biol. 2014; 9:2471-2478.

Dhami G K, Liu H, Galka M, Voss C, Wei R, Muranko K, et al. Dynamic methylation of numb by Set8 regulates its binding to p53 and apoptosis. Mol Cell. 2013; 50(4):565-76.

Ding C, Li R, Peng J, Li S, Guo Z. A polymorphism at the miR-502 binding site in the 3' untranslated region of the Set8 gene is associated with the outcome of small-cell lung cancer. Experimental and therapeutic medicine. 2012; 3(4):689-92.

Guo Z, Wu C, Wang X, Wang C, Zhang R, Shan B. A polymorphism at the miR-502 binding site in the 3'-untranslated region of the histone methyltransferase Set8 is associated with hepatocellular carcinoma outcome. Int J Cancer. 2012; 131(6):1318-22.

Hamamoto R, Saloura V, Nakamura Y. Critical roles of non-histone protein lysine methylation in human tumorigenesis. Nat. Rev. Cancer 2015; 15, 110-124.

Hashemi M, Sheybani-Nasab M, Naderi M, Roodbari F, Taheri M. Association of functional polymorphism at the miR-502-binding site in the 3' untranslated region of the Set8 gene with risk of childhood acute lymphoblastic leukemia, a preliminary report. Tumor Biol. 2014; 35(10): 10375-9.

Ji X, Jin S, Qu X, Li K, Wang H, He F, et al. Lysine-specific demethylase 5C promotes hepatocellular carcinoma cell invasion through inhibition BMP7 expression, BMC Cancer 2015; 26: 801.

Jin H, Zangar R C. Protein modifications as potential biomarkers in breast cancer. Biomark. Insights 2009; 4, 191-200.

Rau R C, Dou Y. Hijacked in cancer: the KMT2(MLL) family of methyltransferases. Nat. Rev. Cancer 2015; 15, 334-346.

Seo J, Lee K J. Post-translational modifications and their biological functions: proteomic analysis and systematic approaches. J. Biochem. Mol. Biol. 2014; 37, 35-44.

Shi X, Kachirskaia 1, Yamaguchi H, West L E, Wen H, Wang E W, et al. Modulation of p53 function by Set8-mediated methylation at lysine 382. Mol Cell. 2007; 27(4):636-46.

Song F, Zheng H, Liu B, Wei S, Dai H, Zhang L, et al. An miR-502-binding site single-nucleotide polymorphism in the 3'-untranslated region of the Set8 gene is associated with early age of breast cancer onset. Clin Cancer Res. 2009; 15(19):6292-300.

Stein J, Majores M, Rohde M, Lim S, Schneider S, Krappe E, et al. KDM5C is overexpressed in prostate cancer and is a prognostic marker for prostate-specific antigen-relapse following radical prostatectomy. Am. J. Pathol. 2014; 184: 2430-2437.

Takawa M, Cho H-S, Hayami S, Toyokawa G, Kogure M, Yamane Y, et al. Histone lysine methyltransferase Set8 promotes carcinogenesis by deregulating PCNA expression. Cancer Res. 2012; 72(13):3217-27.

Valente S, Lepore 1, Dell'Aversana C, Tardugno M, Castellano S, Sbardella G, et al. Identification of PR-SET7 and EZH2 selective inhibitors inducing cell death in human leukemia U937 cells. Biochimie. 2012; 94(11): 2308-13.

Veschi V, Liu Z, Voss T C, Ozbun L, Gryder B, Yan C, et al. Epigenetic siRNA and chemical screens identify Set8 inhibition as a therapeutic strategy for p53 activation in high-risk neuroblastoma. Cancer Cell 2017; 31:50-63.

Vinogradova M, Gehling V S, Gustafson A, Arora S, Tindell C A, et al. (2016). An inhibitor of KDM5 demethylases reduces survival of drug-tolerant cancer cells. Nat. Chem. Biol. 12(7): 531-538.

Wang C, Guo Z, Wu C, Li Y, Kang S. A polymorphism at the miR-502 binding site in the 3' untranslated region of the Set8 gene is associated with the risk of epithelial ovarian cancer. Cancer Genetics. 2012:205(7-8): 373-6.

Wang Q, Wei J, Su P, Gao P. Histone demethylase JARIDIC promotes breast cancer metastasis cells via down regulating BRMS1 expression, Biochem. Biophys. Res. Commun. 2015; 464: 659-666.

Xu J, Yin Z, Gao W, Liu L, Yin Y, Liu P, et al. Genetic variation in a microRNA-502 minding site in Set8 gene confers clinical outcome of non-small cell lung cancer in a Chinese population. PLoS One. 2013; 8(10):e77024.

Xu L, Wu W, Cheng G, Qian M, Hu K, Yin G, et al. Enhancement of proliferation and invasion of gastric cancer cell by KDM5C via decrease in p53 expression. Technol. Cancer Res. Treat. 2017; 16:141-149.

Yang F, Sun L, Li Q, Han X, Lei L, Zhang H, et al. Set8 promotes epithelial mesenchymal transition and confers TWIST dual transcriptional activities. EMBO J. 2012; 31(1):110-23.

Yao L, Li Y, Du F, Han X, Li X, Niu Y, et al. Histone H4 Lys 20 methyltransferase Set8 promotes androgen receptor-mediated transcription activation in prostate cancer. Biochem Biophys Res Commun. 2014; 450(1):692-6.

Zhang X, Wen H, Shi X. Lysine methylation: beyond histones. Acta Biochim. Biophys. Sin. 2012; 44, 14-27.

The invention claimed is:

1. A peptide that binds to KDM5C and consists of the sequence selected from the group consisting of T D T T K T H H H (SEQ ID NO:1); T D T Q K T H H H (SEQ ID NO:2); T D T N K T H H H (SEQ ID NO:3); T E D Q K T H H H (SEQ ID NO:5); T T Q S K T H H H (SEQ ID NO:6); T D T S K T H H H (SEQ ID NO:7); TED TK THHH (SEQ ID NO:8); S D Q Q K T H H H (SEQ ID NO:10); T T Q Q K T H H H (SEQ ID NO:11); S D Q T K T H H H (SEQ ID NO:12); T D D Q K T H H H (SEQ ID NO:13); T E E N K T H H H (SEQ ID NO:14); T E E S K T H H H (SEQ ID NO:15); T T Q T K T H H H (SEQ ID NO:16); T D S T K T H H H (SEQ ID NO:17); S E T Q K T H H H (SEQ ID NO:18); S E T S K T H H H (SEQ ID NO:19); T D D N K T H H H (SEQ ID NO:20); T D T T n T H H H (SEQ ID NO:21); T D T Q n T H H H (SEQ ID NO:22); T D T N n T H H H (SEQ ID NO:23); T E D S n T H H H (SEQ ID NO:24); T E D Q n T H H H (SEQ ID NO:25); T T Q S n T H H H (SEQ ID NO:26); T D T S n T H H H (SEQ ID NO:27); T E D T n T H H H (SEQ ID NO:28); T E E Q n T H H H (SEQ ID NO:29); S D Q Q n T H H H (SEQ ID NO:30); T T Q Q n T H H H (SEQ ID NO:31); S D Q T n T H H H (SEQ ID NO:32); T D D Q n T H H H (SEQ ID NO:33); T E E N n T H H H (SEQ ID NO:34); T E E S n T H H H (SEQ ID NO:35); T T Q T n T H H H (SEQ ID NO:36); T D S T n T H H H (SEQ ID NO:37); S E T Q n T H H H (SEQ ID NO:38); S E T S n T H H H (SEQ ID NO:39); T D D N n T H H H (SEQ ID NO:40); R T K Q T A R K S T G G (SEQ ID NO:41); R T n Q T A R K S T G G (SEQ ID NO:42); G A K R H R K V L R D N I (SEQ ID NO:43) and GA K R H R n V L R D N I (SEQ ID NO:44); wherein n=norLeucine (Nle) or a binding fragment thereof.

2. A conjugate consisting of the peptide of claim 1, coupled directly or via a linker to a cell penetrating peptide.

3. The conjugate of claim 2, wherein said cell penetrating peptide is a TAT cell penetrating peptide.

4. The conjugate of claim 3, wherein said linker is a 6-aminohexanoic acid linker.

5. A peptide consisting of the sequence selected from the group consisting of:

```
                                    (SEQ ID NO: 23)
TDTNnTHHH

                                    (SEQ ID NO: 45)
{6-aminohexanoic acid}GRKKRRQRRRPPQ;

                                (SEQ ID NO: 2)
TDTQKTHHH

                                (SEQ ID NO: 45)
{6-aminohexanoic acid}GRKKRRQRRRPPQ;

                                (SEQ ID NO: 3)
TDTNKTHHH

                                (SEQ ID NO: 45)
{6-aminohexanoic acid}GRKKRRQRRRPPQ;

                                (SEQ ID NO: 27)
TDTSnTHHH

                                (SEQ ID NO: 45)
{6-aminohexanoic acid}GRKKRRQRRRPPQ;

                                (SEQ ID NO: 4)
TEDSKTHHH

                                (SEQ ID NO: 45)
{6-aminohexanoic acid}GRKKRRQRRRPPQ;
```

-continued

```
                                    (SEQ ID NO: 7)
TDTSKTHHH

                                    (SEQ ID NO: 45)
{6-aminohexanoic acid}GRKKRRQRRRPPQ;

                                    (SEQ ID NO: 40)
TDTTnTHHH

                                    (SEQ ID NO: 45)
{6-aminohexanoic acid}GRKKRRQRRRPPQ;

                                    (SEQ ID NO: 25)
TEDQnTHHH

                                    (SEQ ID NO: 45)
{6-aminohexanoic acid}GRKKRRQRRRPPQ;

                                    (SEQ ID NO: 6)
TTQSKTHHH

                                    (SEQ ID NO: 45)
{6-aminohexanoic acid}GRKKRRQRRRPPQ;

                                    (SEQ ID NO: 5)
TEDQKTHHH

                                    (SEQ ID NO: 45)
{6-aminohexanoic acid}GRKKRRQRRRPPQ;

                                    (SEQ ID NO: 44)
GAKRHRnVLRDNI

                                    (SEQ ID NO: 45)
{6-aminohexanoic acid}GRKKRRQRRRPPQ;

                                    (SEQ ID NO: 38)
SETQnTHHH

                                    (SEQ ID NO: 45)
{6-aminohexanoic acid}GRKKRRQRRRPPQ;

                                    (SEQ ID NO: 10)
SDQQKTHHH

                                    (SEQ ID NO: 45)
{6-aminohexanoic acid}GRKKRRQRRRPPQ;

                                    (SEQ ID NO: 23)
TDTNnTHHH

                                    (SEQ ID NO: 49)
{6-aminohexanoic acid}FFLIPKGRRRRRRRRR;

                                    (SEQ ID NO: 2)
TDTQKTHHH

                                    (SEQ ID NO: 49)
{6-aminohexanoic acid}FFLIPKGRRRRRRRRR;

                                    (SEQ ID NO: 3)
TDTNKTHHH

                                    (SEQ ID NO: 49)
{6-aminohexanoic acid}FFLIPKGRRRRRRRRR;

                                    (SEQ ID NO: 27)
TDTSnTHHH

                                    (SEQ ID NO: 49)
{6-aminohexanoic acid}FFLIPKGRRRRRRRRR;

                                    (SEQ ID NO: 4)
TEDSKTHHH

                                    (SEQ ID NO: 49)
{6-aminohexanoic acid}FFLIPKGRRRRRRRRR;

                                    (SEQ ID NO: 7)
TDTSKTHHH
```

-continued (SEQ ID NO: 49)
{6-aminohexanoic acid}FFLIPKGRRRRRRRRR;

(SEQ ID NO: 40)
TDTTnTHHH (SEQ ID NO: 49)
{6-aminohexanoic acid}FFLIPKGRRRRRRRRR;

(SEQ ID NO:)
TEDQnTHHH (SEQ ID NO: 49)
{6-aminohexanoic acid}FFLIPKGRRRRRRRRR;

(SEQ ID NO: 6)
TTQSKTHHH (SEQ ID NO: 49)
{6-aminohexanoic acid}FFLIPKGRRRRRRRRR;

(SEQ ID NO: 5)
TEDQKTHHH (SEQ ID NO: 49)
{6-aminohexanoic acid}FFLIPKGRRRRRRRRR;

(SEQ ID NO: 44)
GAKRHRnVLRDNI (SEQ ID NO: 49)
{6-aminohexanoic acid}FFLIPKGRRRRRRRRR;

(SEQ ID NO: 38)
SETQnTHHH (SEQ ID NO: 49)
{6-aminohexanoic acid}FFLIPKGRRRRRRRRR;

(SEQ ID NO: 10)
SDQQKTHHH (SEQ ID NO: 49)
{6-aminohexanoic acid}FFLIPKGRRRRRRRRR;

(SEQ ID NO: 23)
TDTNnTHHH (SEQ ID NO: 50)
{6-aminohexanoic acid}RRWRRWRRWRR;

(SEQ ID NO: 2)
TDTQKTHHH (SEQ ID NO: 50)
{6-aminohexanoic acid}RRWRRWRRWRR;

(SEQ ID NO: 3)
TDTNKTHHH (SEQ ID NO: 50)
{6-aminohexanoic acid}RRWRRWRRWRR;

-continued (SEQ ID NO: 27)
TDTSnTHHH (SEQ ID NO: 50)
{6-aminohexanoic acid}RRWRRWRRWRR;

(SEQ ID NO: 4)
TEDSKTHHH (SEQ ID NO: 50)
{6-aminohexanoic acid}RRWRRWRRWRR;

(SEQ ID NO: 7)
TDTSKTHHH (SEQ ID NO: 50)
{6-aminohexanoic acid}RRWRRWRRWRR;

(SEQ ID NO: 40)
TDTTnTHHH (SEQ ID NO: 50)
{6-aminohexanoic acid}RRWRRWRRWRR;

(SEQ ID NO:)
TEDQnTHHH (SEQ ID NO: 50)
{6-aminohexanoic acid}RRWRRWRRWRR;

(SEQ ID NO: 6)
TTQSKTHHH (SEQ ID NO: 50)
{6-aminohexanoic acid}RRWRRWRRWRR;

(SEQ ID NO: 5)
TEDQKTHHH (SEQ ID NO: 50)
{6-aminohexanoic acid}RRWRRWRRWRR;

(SEQ ID NO: 44)
GAKRHRnVLRDNI (SEQ ID NO: 50)
{6-aminohexanoic acid}RRWRRWRRWRR;

(SEQ ID NO: 38)
SETQnTHHH (SEQ ID NO: 50)
{6-aminohexanoic acid}RRWRRWRRWRR; and (SEQ ID NO: 10)
SDQQKTHHH (SEQ ID NO: 50)
{6-aminohexanoic acid}RRWRRWRRWRR.

6. The peptide of any one of claim 1, 4, or 5, wherein said peptide inhibits KDM5C activity.

* * * * *

SEQUENCE LISTING

```
<160> NUMBER OF SEQ ID NOS: 68

<210> SEQ ID NO 1
<211> LENGTH: 9
<212> TYPE: PRT
<213> ORGANISM: Artificial Sequence
<220> FEATURE:
<223> OTHER INFORMATION: peptide binding to KDM5C

<400> SEQUENCE: 1

Thr Asp Thr Thr Lys Thr His His His
1               5


<210> SEQ ID NO 2
<211> LENGTH: 9
<212> TYPE: PRT
<213> ORGANISM: Artificial Sequence
<220> FEATURE:
<223> OTHER INFORMATION: peptide binding to KDM5C

<400> SEQUENCE: 2

Thr Asp Thr Gln Lys Thr His His His
1               5


<210> SEQ ID NO 3
<211> LENGTH: 9
<212> TYPE: PRT
<213> ORGANISM: Artificial Sequence
<220> FEATURE:
<223> OTHER INFORMATION: peptide binding to KDM5C

<400> SEQUENCE: 3

Thr Asp Thr Asn Lys Thr His His His
1               5


<210> SEQ ID NO 4
<211> LENGTH: 9
<212> TYPE: PRT
<213> ORGANISM: Artificial Sequence
<220> FEATURE:
<223> OTHER INFORMATION: peptide binding to KDM5C

<400> SEQUENCE: 4

Thr Glu Asp Ser Lys Thr His His His
1               5


<210> SEQ ID NO 5
<211> LENGTH: 9
<212> TYPE: PRT
<213> ORGANISM: Artificial Sequence
<220> FEATURE:
<223> OTHER INFORMATION: peptide binding to KDM5C

<400> SEQUENCE: 5

Thr Glu Asp Gln Lys Thr His His His
1               5


<210> SEQ ID NO 6
<211> LENGTH: 9
<212> TYPE: PRT
<213> ORGANISM: Artificial Sequence
<220> FEATURE:
<223> OTHER INFORMATION: peptide binding to KDM5C

<400> SEQUENCE: 6

Thr Thr Gln Ser Lys Thr His His His
1               5
```

-continued

<210> SEQ ID NO 7
<211> LENGTH: 9
<212> TYPE: PRT
<213> ORGANISM: Artificial Sequence
<220> FEATURE:
<223> OTHER INFORMATION: peptide binding to KDM5C

<400> SEQUENCE: 7

Thr Asp Thr Ser Lys Thr His His His
1               5

<210> SEQ ID NO 8
<211> LENGTH: 9
<212> TYPE: PRT
<213> ORGANISM: Artificial Sequence
<220> FEATURE:
<223> OTHER INFORMATION: peptide binding to KDM5C

<400> SEQUENCE: 8

Thr Glu Asp Thr Lys Thr His His His
1               5

<210> SEQ ID NO 9
<211> LENGTH: 9
<212> TYPE: PRT
<213> ORGANISM: Artificial Sequence
<220> FEATURE:
<223> OTHER INFORMATION: peptide binding to KDM5C

<400> SEQUENCE: 9

Thr Glu Glu Gln Lys Thr His His His
1               5

<210> SEQ ID NO 10
<211> LENGTH: 9
<212> TYPE: PRT
<213> ORGANISM: Artificial Sequence
<220> FEATURE:
<223> OTHER INFORMATION: peptide binding to KDM5C

<400> SEQUENCE: 10

Ser Asp Gln Gln Lys Thr His His His
1               5

<210> SEQ ID NO 11
<211> LENGTH: 9
<212> TYPE: PRT
<213> ORGANISM: Artificial Sequence
<220> FEATURE:
<223> OTHER INFORMATION: peptide binding to KDM5C

<400> SEQUENCE: 11

Thr Thr Gln Gln Lys Thr His His His
1               5

<210> SEQ ID NO 12
<211> LENGTH: 9
<212> TYPE: PRT
<213> ORGANISM: Artificial Sequence
<220> FEATURE:
<223> OTHER INFORMATION: peptide binding to KDM5C

<400> SEQUENCE: 12

Ser Asp Gln Thr Lys Thr His His His
1               5

-continued

<210> SEQ ID NO 13
<211> LENGTH: 9
<212> TYPE: PRT
<213> ORGANISM: Artificial Sequence
<220> FEATURE:
<223> OTHER INFORMATION: peptide binding to KDM5C

<400> SEQUENCE: 13

Thr Asp Asp Gln Lys Thr His His His
1               5

<210> SEQ ID NO 14
<211> LENGTH: 9
<212> TYPE: PRT
<213> ORGANISM: Artificial Sequence
<220> FEATURE:
<223> OTHER INFORMATION: peptide binding to KDM5C

<400> SEQUENCE: 14

Thr Glu Glu Asn Lys Thr His His His
1               5

<210> SEQ ID NO 15
<211> LENGTH: 9
<212> TYPE: PRT
<213> ORGANISM: Artificial Sequence
<220> FEATURE:
<223> OTHER INFORMATION: peptide binding to KDM5C

<400> SEQUENCE: 15

Thr Glu Glu Ser Lys Thr His His His
1               5

<210> SEQ ID NO 16
<211> LENGTH: 9
<212> TYPE: PRT
<213> ORGANISM: Artificial Sequence
<220> FEATURE:
<223> OTHER INFORMATION: peptide binding to KDM5C

<400> SEQUENCE: 16

Thr Thr Gln Thr Lys Thr His His His
1               5

<210> SEQ ID NO 17
<211> LENGTH: 9
<212> TYPE: PRT
<213> ORGANISM: Artificial Sequence
<220> FEATURE:
<223> OTHER INFORMATION: peptide binding to KDM5C

<400> SEQUENCE: 17

Thr Asp Ser Thr Lys Thr His His His
1               5

<210> SEQ ID NO 18
<211> LENGTH: 9
<212> TYPE: PRT
<213> ORGANISM: Artificial Sequence
<220> FEATURE:
<223> OTHER INFORMATION: peptide binding to KDM5C

<400> SEQUENCE: 18

Ser Glu Thr Gln Lys Thr His His His
1               5

-continued

<210> SEQ ID NO 19
<211> LENGTH: 9
<212> TYPE: PRT
<213> ORGANISM: Artificial Sequence
<220> FEATURE:
<223> OTHER INFORMATION: peptide binding to KDM5C

<400> SEQUENCE: 19

Ser Glu Thr Ser Lys Thr His His His
1 5

<210> SEQ ID NO 20
<211> LENGTH: 9
<212> TYPE: PRT
<213> ORGANISM: Artificial Sequence
<220> FEATURE:
<223> OTHER INFORMATION: peptide binding to KDM5C

<400> SEQUENCE: 20

Thr Asp Asp Asn Lys Thr His His His
1 5

<210> SEQ ID NO 21
<211> LENGTH: 9
<212> TYPE: PRT
<213> ORGANISM: Artificial Sequence
<220> FEATURE:
<223> OTHER INFORMATION: peptide binding to KDM5C
<220> FEATURE:
<221> NAME/KEY: MISC_FEATURE
<222> LOCATION: (5)..(5)
<223> OTHER INFORMATION: norLeucine (Nle)

<400> SEQUENCE: 21

Thr Asp Thr Thr Xaa Thr His His His
1 5

<210> SEQ ID NO 22
<211> LENGTH: 9
<212> TYPE: PRT
<213> ORGANISM: Artificial Sequence
<220> FEATURE:
<223> OTHER INFORMATION: peptide binding to KDM5C
<220> FEATURE:
<221> NAME/KEY: MISC_FEATURE
<222> LOCATION: (5)..(5)
<223> OTHER INFORMATION: norLeucine (Nle)

<400> SEQUENCE: 22

Thr Asp Thr Gln Xaa Thr His His His
1 5

<210> SEQ ID NO 23
<211> LENGTH: 9
<212> TYPE: PRT
<213> ORGANISM: Artificial Sequence
<220> FEATURE:
<223> OTHER INFORMATION: peptide binding to KDM5C
<220> FEATURE:
<221> NAME/KEY: MISC_FEATURE
<222> LOCATION: (5)..(5)
<223> OTHER INFORMATION: norLeucine (Nle)

<400> SEQUENCE: 23

Thr Asp Thr Asn Xaa Thr His His His
1 5

<210> SEQ ID NO 24
<211> LENGTH: 9

<212> TYPE: PRT
<213> ORGANISM: Artificial Sequence
<220> FEATURE:
<223> OTHER INFORMATION: peptide binding to KDM5C
<220> FEATURE:
<221> NAME/KEY: MISC_FEATURE
<222> LOCATION: (5)..(5)
<223> OTHER INFORMATION: norLeucine (Nle)

<400> SEQUENCE: 24

Thr Glu Asp Ser Xaa Thr His His His
1 5

<210> SEQ ID NO 25
<211> LENGTH: 9
<212> TYPE: PRT
<213> ORGANISM: Artificial Sequence
<220> FEATURE:
<223> OTHER INFORMATION: peptide binding to KDM5C
<220> FEATURE:
<221> NAME/KEY: MISC_FEATURE
<222> LOCATION: (5)..(5)
<223> OTHER INFORMATION: norLeucine (Nle)

<400> SEQUENCE: 25

Thr Glu Asp Gln Xaa Thr His His His
1 5

<210> SEQ ID NO 26
<211> LENGTH: 9
<212> TYPE: PRT
<213> ORGANISM: Artificial Sequence
<220> FEATURE:
<223> OTHER INFORMATION: peptide binding to KDM5C
<220> FEATURE:
<221> NAME/KEY: MISC_FEATURE
<222> LOCATION: (5)..(5)
<223> OTHER INFORMATION: norLeucine (Nle)

<400> SEQUENCE: 26

Thr Thr Gln Ser Xaa Thr His His His
1 5

<210> SEQ ID NO 27
<211> LENGTH: 9
<212> TYPE: PRT
<213> ORGANISM: Artificial Sequence
<220> FEATURE:
<223> OTHER INFORMATION: peptide binding to KDM5C
<220> FEATURE:
<221> NAME/KEY: MISC_FEATURE
<222> LOCATION: (5)..(5)
<223> OTHER INFORMATION: norLeucine (Nle)

<400> SEQUENCE: 27

Thr Asp Thr Ser Xaa Thr His His His
1 5

<210> SEQ ID NO 28
<211> LENGTH: 9
<212> TYPE: PRT
<213> ORGANISM: Artificial Sequence
<220> FEATURE:
<223> OTHER INFORMATION: peptide binding to KDM5C
<220> FEATURE:
<221> NAME/KEY: MISC_FEATURE
<222> LOCATION: (5)..(5)
<223> OTHER INFORMATION: norLeucine (Nle)

<400> SEQUENCE: 28

-continued

```
Thr Glu Asp Thr Xaa Thr His His His
1               5


<210> SEQ ID NO 29
<211> LENGTH: 9
<212> TYPE: PRT
<213> ORGANISM: Artificial Sequence
<220> FEATURE:
<223> OTHER INFORMATION: peptide binding to KDM5C
<220> FEATURE:
<221> NAME/KEY: MISC_FEATURE
<222> LOCATION: (5)..(5)
<223> OTHER INFORMATION: norLeucine (Nle)

<400> SEQUENCE: 29

Thr Glu Glu Gln Xaa Thr His His His
1               5


<210> SEQ ID NO 30
<211> LENGTH: 9
<212> TYPE: PRT
<213> ORGANISM: Artificial Sequence
<220> FEATURE:
<223> OTHER INFORMATION: peptide binding to KDM5C
<220> FEATURE:
<221> NAME/KEY: MISC_FEATURE
<222> LOCATION: (5)..(5)
<223> OTHER INFORMATION: norLeucine (Nle)

<400> SEQUENCE: 30

Ser Asp Gln Gln Xaa Thr His His His
1               5


<210> SEQ ID NO 31
<211> LENGTH: 9
<212> TYPE: PRT
<213> ORGANISM: Artificial Sequence
<220> FEATURE:
<223> OTHER INFORMATION: peptide binding to KDM5C
<220> FEATURE:
<221> NAME/KEY: MISC_FEATURE
<222> LOCATION: (5)..(5)
<223> OTHER INFORMATION: norLeucine (Nle)

<400> SEQUENCE: 31

Thr Thr Gln Gln Xaa Thr His His His
1               5


<210> SEQ ID NO 32
<211> LENGTH: 9
<212> TYPE: PRT
<213> ORGANISM: Artificial Sequence
<220> FEATURE:
<223> OTHER INFORMATION: peptide binding to KDM5C
<220> FEATURE:
<221> NAME/KEY: MISC_FEATURE
<222> LOCATION: (5)..(5)
<223> OTHER INFORMATION: norLeucine (Nle)

<400> SEQUENCE: 32

Ser Asp Gln Thr Xaa Thr His His His
1               5


<210> SEQ ID NO 33
<211> LENGTH: 9
<212> TYPE: PRT
<213> ORGANISM: Artificial Sequence
<220> FEATURE:
<223> OTHER INFORMATION: peptide binding to KDM5C
<220> FEATURE:
```

-continued

<221> NAME/KEY: MISC_FEATURE
<222> LOCATION: (5)..(5)
<223> OTHER INFORMATION: norLeucine (Nle)

<400> SEQUENCE: 33

Thr Asp Asp Gln Xaa Thr His His His
1               5

<210> SEQ ID NO 34
<211> LENGTH: 9
<212> TYPE: PRT
<213> ORGANISM: Artificial Sequence
<220> FEATURE:
<223> OTHER INFORMATION: peptide binding to KDM5C
<220> FEATURE:
<221> NAME/KEY: MISC_FEATURE
<222> LOCATION: (5)..(5)
<223> OTHER INFORMATION: norLeucine (Nle)

<400> SEQUENCE: 34

Thr Glu Glu Asn Xaa Thr His His His
1               5

<210> SEQ ID NO 35
<211> LENGTH: 9
<212> TYPE: PRT
<213> ORGANISM: Artificial Sequence
<220> FEATURE:
<223> OTHER INFORMATION: peptide binding to KDM5C
<220> FEATURE:
<221> NAME/KEY: MISC_FEATURE
<222> LOCATION: (5)..(5)
<223> OTHER INFORMATION: norLeucine (Nle)

<400> SEQUENCE: 35

Thr Glu Glu Ser Xaa Thr His His His
1               5

<210> SEQ ID NO 36
<211> LENGTH: 9
<212> TYPE: PRT
<213> ORGANISM: Artificial Sequence
<220> FEATURE:
<223> OTHER INFORMATION: peptide binding to KDM5C
<220> FEATURE:
<221> NAME/KEY: MISC_FEATURE
<222> LOCATION: (5)..(5)
<223> OTHER INFORMATION: norLeucine (Nle)

<400> SEQUENCE: 36

Thr Thr Gln Thr Xaa Thr His His His
1               5

<210> SEQ ID NO 37
<211> LENGTH: 9
<212> TYPE: PRT
<213> ORGANISM: Artificial Sequence
<220> FEATURE:
<223> OTHER INFORMATION: peptide binding to KDM5C
<220> FEATURE:
<221> NAME/KEY: MISC_FEATURE
<222> LOCATION: (5)..(5)
<223> OTHER INFORMATION: norLeucine (Nle)

<400> SEQUENCE: 37

Thr Asp Ser Thr Xaa Thr His His His
1               5

<210> SEQ ID NO 38

-continued

<211> LENGTH: 9
<212> TYPE: PRT
<213> ORGANISM: Artificial Sequence
<220> FEATURE:
<223> OTHER INFORMATION: peptide binding to KDM5C
<220> FEATURE:
<221> NAME/KEY: MISC_FEATURE
<222> LOCATION: (5)..(5)
<223> OTHER INFORMATION: norLeucine (Nle)

<400> SEQUENCE: 38

Ser Glu Thr Gln Xaa Thr His His His
1               5

<210> SEQ ID NO 39
<211> LENGTH: 9
<212> TYPE: PRT
<213> ORGANISM: Artificial Sequence
<220> FEATURE:
<223> OTHER INFORMATION: peptide binding to KDM5C
<220> FEATURE:
<221> NAME/KEY: MISC_FEATURE
<222> LOCATION: (5)..(5)
<223> OTHER INFORMATION: norLeucine (Nle)

<400> SEQUENCE: 39

Ser Glu Thr Ser Xaa Thr His His His
1               5

<210> SEQ ID NO 40
<211> LENGTH: 9
<212> TYPE: PRT
<213> ORGANISM: Artificial Sequence
<220> FEATURE:
<223> OTHER INFORMATION: peptide binding to KDM5C
<220> FEATURE:
<221> NAME/KEY: MISC_FEATURE
<222> LOCATION: (5)..(5)
<223> OTHER INFORMATION: norLeucine (Nle)

<400> SEQUENCE: 40

Thr Asp Asp Asn Xaa Thr His His His
1               5

<210> SEQ ID NO 41
<211> LENGTH: 12
<212> TYPE: PRT
<213> ORGANISM: Artificial Sequence
<220> FEATURE:
<223> OTHER INFORMATION: peptide binding to KDM5C

<400> SEQUENCE: 41

Arg Thr Lys Gln Thr Ala Arg Lys Ser Thr Gly Gly
1               5                   10

<210> SEQ ID NO 42
<211> LENGTH: 12
<212> TYPE: PRT
<213> ORGANISM: Artificial Sequence
<220> FEATURE:
<223> OTHER INFORMATION: peptide binding to KDM5C

<400> SEQUENCE: 42

Arg Thr Asn Gln Thr Ala Arg Lys Ser Thr Gly Gly
1               5                   10

<210> SEQ ID NO 43
<211> LENGTH: 13
<212> TYPE: PRT

-continued

```
<213> ORGANISM: Artificial Sequence
<220> FEATURE:
<223> OTHER INFORMATION: peptide binding to KDM5C

<400> SEQUENCE: 43

Gly Ala Lys Arg His Arg Lys Val Leu Arg Asp Asn Ile
1               5                   10


<210> SEQ ID NO 44
<211> LENGTH: 13
<212> TYPE: PRT
<213> ORGANISM: Artificial Sequence
<220> FEATURE:
<223> OTHER INFORMATION: peptide binding to KDM5C
<220> FEATURE:
<221> NAME/KEY: misc_feature
<222> LOCATION: (7)..(7)
<223> OTHER INFORMATION: Xaa can be any naturally occurring amino acid

<400> SEQUENCE: 44

Gly Ala Lys Arg His Arg Xaa Val Leu Arg Asp Asn Ile
1               5                   10


<210> SEQ ID NO 45
<211> LENGTH: 13
<212> TYPE: PRT
<213> ORGANISM: Artificial Sequence
<220> FEATURE:
<223> OTHER INFORMATION: TAT48-60

<400> SEQUENCE: 45

Gly Arg Lys Lys Arg Arg Gln Arg Arg Arg Pro Pro Gln
1               5                   10


<210> SEQ ID NO 46
<211> LENGTH: 9
<212> TYPE: PRT
<213> ORGANISM: Artificial Sequence
<220> FEATURE:
<223> OTHER INFORMATION: Penetratin, pAntp(43-58)

<400> SEQUENCE: 46

Arg Lys Lys Arg Arg Gln Arg Arg Arg
1               5


<210> SEQ ID NO 47
<211> LENGTH: 16
<212> TYPE: PRT
<213> ORGANISM: Artificial Sequence
<220> FEATURE:
<223> OTHER INFORMATION: Penetratin, pAntp(43-58)

<400> SEQUENCE: 47

Arg Gln Ile Lys Ile Trp Phe Gln Asn Arg Arg Met Lys Trp Lys Lys
1               5                   10                  15


<210> SEQ ID NO 48
<211> LENGTH: 19
<212> TYPE: PRT
<213> ORGANISM: Artificial Sequence
<220> FEATURE:
<223> OTHER INFORMATION: DPV1047

<400> SEQUENCE: 48

Val Lys Arg Gly Leu Lys Leu Arg His Val Arg Pro Arg Val Thr Arg
1               5                   10                  15

Met Asp Val
```

```
<210> SEQ ID NO 49
<211> LENGTH: 16
<212> TYPE: PRT
<213> ORGANISM: Artificial Sequence
<220> FEATURE:
<223> OTHER INFORMATION: PR9

<400> SEQUENCE: 49

Phe Phe Leu Ile Pro Lys Gly Arg Arg Arg Arg Arg Arg Arg Arg Arg
1               5                   10                  15


<210> SEQ ID NO 50
<211> LENGTH: 11
<212> TYPE: PRT
<213> ORGANISM: Artificial Sequence
<220> FEATURE:
<223> OTHER INFORMATION: Mut6DPT (CPP)

<400> SEQUENCE: 50

Arg Arg Trp Arg Arg Trp Arg Arg Trp Arg Arg
1               5                   10


<210> SEQ ID NO 51
<211> LENGTH: 27
<212> TYPE: PRT
<213> ORGANISM: Artificial Seequence
<220> FEATURE:
<223> OTHER INFORMATION: MPG

<400> SEQUENCE: 51

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25


<210> SEQ ID NO 52
<211> LENGTH: 21
<212> TYPE: PRT
<213> ORGANISM: Artificial Sequence
<220> FEATURE:
<223> OTHER INFORMATION: Pep-1

<400> SEQUENCE: 52

Lys Glu Thr Trp Trp Glu Thr Trp Trp Thr Glu Trp Ser Gln Pro Lys
1               5                   10                  15

Lys Lys Arg Lys Val
            20


<210> SEQ ID NO 53
<211> LENGTH: 18
<212> TYPE: PRT
<213> ORGANISM: Artificial Sequence
<220> FEATURE:
<223> OTHER INFORMATION: pVEC

<400> SEQUENCE: 53

Leu Leu Ile Ile Leu Arg Arg Arg Ile Arg Lys Gln Ala His Ala His
1               5                   10                  15

Ser Lys


<210> SEQ ID NO 54
<211> LENGTH: 22
<212> TYPE: PRT
<213> ORGANISM: Artificial Sequence
```

-continued

<220> FEATURE:
<223> OTHER INFORMATION: ARF(1-22)

<400> SEQUENCE: 54

Met Val Arg Arg Phe Leu Val Thr Leu Arg Ile Arg Arg Ala Cys Gly
1 5 10 15

Pro Pro Arg Val Arg Val
20

<210> SEQ ID NO 55
<211> LENGTH: 28
<212> TYPE: PRT
<213> ORGANISM: Artificial Sequence
<220> FEATURE:
<223> OTHER INFORMATION: BPrPr(1-28)

<400> SEQUENCE: 55

Met Val Lys Ser Lys Ile Gly Ser Trp Ile Leu Val Leu Phe Val Ala
1 5 10 15

Met Trp Ser Asp Val Gly Leu Cys Lys Lys Arg Pro
20 25

<210> SEQ ID NO 56
<211> LENGTH: 18
<212> TYPE: PRT
<213> ORGANISM: Artificial Sequence
<220> FEATURE:
<223> OTHER INFORMATION: MAP

<400> SEQUENCE: 56

Lys Leu Ala Leu Lys Leu Ala Leu Lys Ala Leu Lys Ala Ala Leu Lys
1 5 10 15

Leu Ala

<210> SEQ ID NO 57
<211> LENGTH: 27
<212> TYPE: PRT
<213> ORGANISM: Artificial Sequence
<220> FEATURE:
<223> OTHER INFORMATION: Transportan

<400> SEQUENCE: 57

Gly Trp Thr Leu Asn Ser Ala Gly Tyr Leu Leu Gly Lys Ile Asn Leu
1 5 10 15

Lys Ala Leu Ala Ala Leu Ala Lys Lys Ile Leu
20 25

<210> SEQ ID NO 58
<211> LENGTH: 28
<212> TYPE: PRT
<213> ORGANISM: Artificial Sequence
<220> FEATURE:
<223> OTHER INFORMATION: p28

<400> SEQUENCE: 58

Leu Ser Thr Ala Ala Asp Met Gln Gly Val Val Thr Asp Gly Met Ala
1 5 10 15

Ser Gly Leu Asp Lys Asp Tyr Leu Lys Pro Asp Asp
20 25

<210> SEQ ID NO 59
<211> LENGTH: 26
<212> TYPE: PRT
<213> ORGANISM: Artificial Sequence

<220> FEATURE:
<223> OTHER INFORMATION: VT5

<400> SEQUENCE: 59

Asp Pro Lys Gly Asp Pro Lys Gly Val Thr Val Thr Val Thr Val Thr
1               5                   10                  15

Val Thr Gly Lys Gly Asp Pro Lys Pro Asp
            20                  25

<210> SEQ ID NO 60
<211> LENGTH: 24
<212> TYPE: PRT
<213> ORGANISM: Artificial Sequence
<220> FEATURE:
<223> OTHER INFORMATION: Bac 7 (Bac 1-24)

<400> SEQUENCE: 60

Arg Arg Ile Arg Pro Arg Pro Pro Arg Leu Pro Arg Pro Arg Pro Arg
1               5                   10                  15

Pro Leu Pro Phe Pro Arg Pro Gly
            20

<210> SEQ ID NO 61
<211> LENGTH: 17
<212> TYPE: PRT
<213> ORGANISM: Artificial Sequence
<220> FEATURE:
<223> OTHER INFORMATION: C105Y

<400> SEQUENCE: 61

Cys Ser Ile Pro Pro Glu Val Lys Phe Asn Lys Pro Phe Val Tyr Leu
1               5                   10                  15

Ile

<210> SEQ ID NO 62
<211> LENGTH: 6
<212> TYPE: PRT
<213> ORGANISM: Artificial Sequence
<220> FEATURE:
<223> OTHER INFORMATION: PFVYLI

<400> SEQUENCE: 62

Pro Phe Val Tyr Leu Ile
1               5

<210> SEQ ID NO 63
<211> LENGTH: 15
<212> TYPE: PRT
<213> ORGANISM: Artificial Sequence
<220> FEATURE:
<223> OTHER INFORMATION: Pep-7

<400> SEQUENCE: 63

Ser Asp Leu Trp Glu Met Met Met Val Ser Leu Ala Cys Gln Tyr
1               5                   10                  15

<210> SEQ ID NO 64
<211> LENGTH: 765
<212> TYPE: PRT
<213> ORGANISM: Artificial Sequence
<220> FEATURE:
<223> OTHER INFORMATION: The sequence of recombinant KDM5C

<400> SEQUENCE: 64

Met Glu Pro Gly Ser Asp Asp Phe Leu Pro Pro Pro Glu Cys Pro Val

-continued

```
1               5                   10                  15

Phe Glu Pro Ser Trp Ala Glu Phe Arg Asp Pro Leu Gly Tyr Ile Ala
            20                  25                  30

Lys Ile Arg Pro Ile Ala Glu Lys Ser Gly Ile Cys Lys Ile Arg Pro
        35                  40                  45

Pro Ala Asp Trp Gln Pro Pro Phe Ala Val Glu Val Asp Asn Phe Arg
    50                  55                  60

Phe Thr Pro Arg Ile Gln Arg Leu Asn Glu Leu Glu Ala Gln Thr Arg
65                  70                  75                  80

Val Lys Leu Asn Tyr Leu Asp Gln Ile Ala Lys Phe Trp Glu Ile Gln
                85                  90                  95

Gly Ser Ser Leu Lys Ile Pro Asn Val Glu Arg Arg Ile Leu Asp Leu
            100                 105                 110

Tyr Ser Leu Ser Lys Ile Val Val Glu Glu Gly Gly Tyr Glu Ala Ile
        115                 120                 125

Cys Lys Asp Arg Arg Trp Ala Arg Val Ala Gln Arg Leu Asn Tyr Pro
    130                 135                 140

Pro Gly Lys Asn Ile Gly Ser Leu Leu Arg Ser His Tyr Glu Arg Ile
145                 150                 155                 160

Val Tyr Pro Tyr Glu Met Tyr Gln Ser Gly Ala Asn Leu Val Gln Cys
                165                 170                 175

Asn Thr Arg Pro Phe Asp Asn Glu Glu Lys Asp Lys Glu Tyr Lys Pro
            180                 185                 190

His Ser Ile Pro Leu Arg Gln Ser Val Gln Pro Ser Lys Phe Asn Ser
        195                 200                 205

Tyr Gly Arg Arg Ala Lys Arg Leu Gln Pro Asp Pro Glu Pro Thr Glu
    210                 215                 220

Glu Asp Ile Glu Lys Asn Pro Glu Leu Lys Lys Leu Gln Ile Tyr Gly
225                 230                 235                 240

Ala Gly Pro Lys Met Met Gly Leu Gly Leu Met Ala Lys Asp Lys Thr
                245                 250                 255

Leu Arg Lys Lys Asp Lys Glu Gly Pro Glu Cys Pro Pro Thr Val Val
            260                 265                 270

Val Lys Glu Glu Leu Gly Gly Asp Val Lys Val Glu Ser Thr Ser Pro
        275                 280                 285

Lys Thr Phe Leu Glu Ser Lys Glu Glu Leu Ser His Ser Pro Glu Pro
    290                 295                 300

Cys Thr Lys Met Thr Met Arg Leu Arg Arg Asn His Ser Asn Ala Gln
305                 310                 315                 320

Phe Ile Glu Ser Tyr Val Cys Arg Met Cys Ser Arg Gly Asp Glu Asp
                325                 330                 335

Asp Lys Leu Leu Leu Cys Asp Gly Cys Asp Asp Asn Tyr His Ile Phe
            340                 345                 350

Cys Leu Leu Pro Pro Leu Pro Glu Ile Pro Lys Gly Val Trp Arg Cys
        355                 360                 365

Pro Lys Cys Val Met Ala Glu Cys Lys Arg Pro Pro Glu Ala Phe Gly
    370                 375                 380

Phe Glu Gln Ala Thr Arg Glu Tyr Thr Leu Gln Ser Phe Gly Glu Met
385                 390                 395                 400

Ala Asp Ser Phe Lys Ala Asp Tyr Phe Asn Met Pro Val His Met Val
                405                 410                 415

Pro Thr Glu Leu Val Glu Lys Glu Phe Trp Arg Leu Val Asn Ser Ile
            420                 425                 430
```

-continued

```
Glu Glu Asp Val Thr Val Glu Tyr Gly Ala Asp Ile His Ser Lys Glu
        435                 440                 445

Phe Gly Ser Gly Phe Pro Val Ser Asp Ser Lys Arg His Leu Thr Pro
    450                 455                 460

Glu Glu Glu Glu Tyr Ala Thr Ser Gly Trp Asn Leu Asn Val Met Pro
465                 470                 475                 480

Val Leu Glu Gln Ser Val Leu Cys His Ile Asn Ala Asp Ile Ser Gly
                485                 490                 495

Met Lys Val Pro Trp Leu Tyr Val Gly Met Val Phe Ser Ala Phe Cys
            500                 505                 510

Trp His Ile Glu Asp His Trp Ser Tyr Ser Ile Asn Tyr Leu His Trp
        515                 520                 525

Gly Glu Pro Lys Thr Trp Tyr Gly Val Pro Ser Leu Ala Ala Glu His
    530                 535                 540

Leu Glu Glu Val Met Lys Lys Leu Thr Pro Glu Leu Phe Asp Ser Gln
545                 550                 555                 560

Pro Asp Leu Leu His Gln Leu Val Thr Leu Met Asn Pro Asn Thr Leu
                565                 570                 575

Met Ser His Gly Val Pro Val Val Arg Thr Asn Gln Cys Ala Gly Glu
            580                 585                 590

Phe Val Ile Thr Phe Pro Arg Ala Tyr His Ser Gly Phe Asn Gln Gly
        595                 600                 605

Tyr Asn Phe Ala Glu Ala Val Asn Phe Cys Thr Ala Asp Trp Leu Pro
    610                 615                 620

Ala Gly Arg Gln Cys Ile Glu His Tyr Arg Arg Leu Arg Arg Tyr Cys
625                 630                 635                 640

Val Phe Ser His Glu Glu Leu Ile Cys Lys Met Ala Ala Cys Pro Glu
                645                 650                 655

Lys Leu Asp Leu Asn Leu Ala Ala Ala Val His Lys Glu Met Phe Ile
            660                 665                 670

Met Val Gln Glu Glu Arg Arg Leu Arg Lys Ala Leu Leu Glu Lys Gly
        675                 680                 685

Ile Thr Glu Ala Glu Arg Glu Ala Phe Glu Leu Leu Pro Asp Asp Glu
    690                 695                 700

Arg Gln Cys Ile Lys Cys Lys Thr Thr Cys Phe Leu Ser Ala Leu Ala
705                 710                 715                 720

Cys Tyr Asp Cys Pro Asp Gly Leu Val Cys Leu Ser His Ile Asn Asp
                725                 730                 735

Leu Cys Lys Cys Ser Ser Ser Arg Gln Tyr Leu Arg Tyr Arg Tyr Thr
            740                 745                 750

Leu Asp Glu Leu Pro Ala Met Leu His Lys Leu Lys Val
        755                 760                 765
```

<210> SEQ ID NO 65
<211> LENGTH: 9
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (1)..(1)
<223> OTHER INFORMATION: T or S
<220> FEATURE:
<221> NAME/KEY: MISC_FEATURE
<222> LOCATION: (2)..(2)
<223> OTHER INFORMATION: D, E or I
<220> FEATURE:
<221> NAME/KEY: MISC_FEATURE
<222> LOCATION: (3)..(3)
<223> OTHER INFORMATION: T, D or Q
<220> FEATURE:
<221> NAME/KEY: MISC_FEATURE
<222> LOCATION: (4)..(4)
<223> OTHER INFORMATION: Q, S, N or T
<220> FEATURE:
<221> NAME/KEY: MISC_FEATURE
<222> LOCATION: (5)..(5)
<223> OTHER INFORMATION: K or Nle

<400> SEQUENCE: 65

Xaa Xaa Xaa Xaa Xaa Thr His His His
1               5

<210> SEQ ID NO 66
<211> LENGTH: 9
<212> TYPE: PRT
<213> ORGANISM: Artificial Sequence
<220> FEATURE:
<223> OTHER INFORMATION: KDM5C binding peptide
<220> FEATURE:
<221> NAME/KEY: MISC_FEATURE
<222> LOCATION: (2)..(2)
<223> OTHER INFORMATION: K, G, L, Q, V, E, H or I
<220> FEATURE:
<221> NAME/KEY: MISC_FEATURE
<222> LOCATION: (3)..(3)
<223> OTHER INFORMATION: I, L, V or D
<220> FEATURE:
<221> NAME/KEY: MISC_FEATURE
<222> LOCATION: (4)..(4)
<223> OTHER INFORMATION: L, M, V, F or S
<220> FEATURE:
<221> NAME/KEY: MISC_FEATURE
<222> LOCATION: (5)..(5)
<223> OTHER INFORMATION: V or K
<220> FEATURE:
<221> NAME/KEY: MISC_FEATURE
<222> LOCATION: (6)..(6)
<223> OTHER INFORMATION: V, G, R, L, K, F, H, T, A, P, I or N

<400> SEQUENCE: 66

Thr Xaa Xaa Xaa Xaa Xaa His His His
1               5

<210> SEQ ID NO 67
<211> LENGTH: 5
<212> TYPE: PRT
<213> ORGANISM: Artificial Sequence
<220> FEATURE:
<223> OTHER INFORMATION: Linker

<400> SEQUENCE: 67

Gly Gly Gly Gly Ser
1               5

<210> SEQ ID NO 68
<211> LENGTH: 5
<212> TYPE: PRT
<213> ORGANISM: Artificial Sequence
<220> FEATURE:
<223> OTHER INFORMATION: Linker

<400> SEQUENCE: 68

Glu Ala Ala Ala Lys
1               5